United States Patent
Jeannin et al.

(10) Patent No.: US 11,666,548 B2
(45) Date of Patent: Jun. 6, 2023

(54) PARENTERAL NUTRITION FORMULATION

(71) Applicants: BAXTER INTERNATIONAL INC., Deerfield, IL (US); BAXTER HEALTHCARE SA, Glattpark (CH)

(72) Inventors: Laurent Christian Jeannin, Braine l'Alleud (BE); Mary Hise Brown, Vernon Hills, IL (US); Julien Andre Roger Hecq, Uccle (BE); Gary P. Zaloga, Evanston, IL (US); Kelly Tappenden, Decatur, GA (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

(21) Appl. No.: 16/893,807

(22) Filed: Jun. 5, 2020

(65) Prior Publication Data
US 2021/0378998 A1 Dec. 9, 2021

(51) Int. Cl.
| | | |
|---|---|---|
| *A61K 31/198* | (2006.01) | |
| *A61J 1/05* | (2006.01) | |
| *A23L 33/18* | (2016.01) | |
| *A23L 33/175* | (2016.01) | |
| *A23L 33/125* | (2016.01) | |
| *A23L 33/00* | (2016.01) | |
| *A61K 47/26* | (2006.01) | |
| *A61K 47/42* | (2017.01) | |
| *A61K 47/44* | (2017.01) | |
| *A23L 33/115* | (2016.01) | |
| *A23L 33/16* | (2016.01) | |
| *A23L 33/15* | (2016.01) | |
| *A61K 9/00* | (2006.01) | |

(52) U.S. Cl.
CPC .......... *A61K 31/198* (2013.01); *A23L 33/125* (2016.08); *A23L 33/175* (2016.08); *A23L 33/18* (2016.08); *A23L 33/40* (2016.08); *A61J 1/05* (2013.01); *A61K 47/26* (2013.01); *A61K 47/42* (2013.01); *A61K 47/44* (2013.01); *A23L 33/115* (2016.08); *A23L 33/15* (2016.08); *A23L 33/16* (2016.08); *A61K 9/0029* (2013.01)

(58) Field of Classification Search
CPC ....... A61K 31/198; A61K 47/26; A23L 33/18; A61J 1/05
USPC ....................................................... 424/400
See application file for complete search history.

(56) References Cited

U.S. PATENT DOCUMENTS

| | | | | |
|---|---|---|---|---|
| 5,858,365 A | * | 1/1999 | Faller | A61P 7/00 424/184.1 |
| 5,919,822 A | | 7/1999 | Cotter et al. | |
| 7,947,303 B2 | * | 5/2011 | Kessler | A23L 33/175 424/439 |
| 2007/0092579 A1 | * | 4/2007 | Trouilly | A61K 9/0019 424/601 |
| 2009/0111856 A1 | * | 4/2009 | Brulls | A61P 1/04 514/338 |
| 2010/0222271 A1 | | 9/2010 | Nu | |
| 2018/0000764 A1 | * | 1/2018 | Hern Ndez Miramontes et al. | A61K 33/06 |
| 2018/0326149 A1 | * | 11/2018 | Lipschultz | G16H 50/20 |
| 2019/0314307 A1 | | 10/2019 | Goosens et al. | |

FOREIGN PATENT DOCUMENTS

| | | | | |
|---|---|---|---|---|
| WO | 95/11699 | 5/1995 | | |
| WO | 2019/211605 | 11/2019 | | |
| WO | WO-2019211605 A1 | * | 11/2019 | ............. A23L 33/40 |
| WO | 2019/232044 | 12/2019 | | |
| WO | 2019232054 | 12/2019 | | |

OTHER PUBLICATIONS

Murakoshi et al., Journal of Parenteral and Enteral Nutrition 2011; 35(4): 465-472.
Koruda et al., Am J Clin Nutr 1990; 51 685-689.
Pratt et al., Short-Chain Fatty Acid-Supplemented Total Parenteral Nutrition Improves Nonspecific Immunity After Intestinal Resection in Rats. Journal of Parenteral and Enteral Nutrition 1996; 20(4):264-271.
Tappenden et al., Short-Chain Fatty Acid-Supplemented Total Parenteral Nutrition Enhances Functional Adaptation to Intestinal Resection in Rats. Gastroenterology 1997; 112:792-802.
Milo et al., Effects of Short-Chain Fatty Acid-Supplemented Total Parenteral Nutrition on Intestinal Pro-Inflammatory Cytokine Abundance. Digestive Diseases and Sciences 2002; 47:2049-2055.
Bartholome et al., Supplementation of Total Parenteral Nutrition With Butyrate Acutely Increases Structural Aspects of Intestinal Adaptation After an 80% Jejunoileal Resection in Neonatal Piglets. Journal of Parenteral and Enteral Nutrition 2004; 28(4):210-223.
Jirsova et al., The Effect of Butyrate-Supplemented Parenteral Nutrition on Intestinal Defence Mechanisms and the Parenteral Nutrition-Induced Shift in the Gut Microbiota in the Rat Model. BioMed Research International 2019 2019:1-14.
Vianello S, Yu H, Voisin V, et al. Arginine butyrate: a therapeutic candidate for Duchenne muscular dystrophy. FASEB J. 2013;27(6):2256-2269.
McMahon et al., A randomized phase II trial of Arginine Butyrate with standard local therapy in refractory sickle cell leg ulcers, bjh 2010; 151(5):516-524.

(Continued)

*Primary Examiner* — Johann R Richter
*Assistant Examiner* — Courtney A Brown
(74) *Attorney, Agent, or Firm* — K&L Gates LLP

(57) ABSTRACT

The present disclosure relates to parenteral nutrition formulations, including ready-to-use parenteral nutrition formulations which are reconstituted from multi-chamber containers and amino acid formulations. More particularly, the present disclosure is directed to formulations comprising butyrate derivatives, specifically arginine butyrate, for use with adult or pediatric patients. The disclosure further provides for methods of reducing or preventing systemic and local inflammation of patients receiving parenteral nutrition, and methods of maintaining or ameliorating their systemic immunity and local immunity, as well as the patients' gut barrier functions.

39 Claims, 19 Drawing Sheets

(56) References Cited

OTHER PUBLICATIONS

Douillard et al., Phase I trial of interleukin-2 and high-dose arginine butyrate in metastatic colorectal cancer. Cancer Immunology Immunotherapy 2000;49:56-61.

Thomson et al., The Ussing chamber system for measuring intestinal permeability in health and disease, BMC Gastroenterology 2019; 19:98.

ISR for PCT/US2021/034497 dated Sep. 21, 2021 (17 pages).

Baxter: "Product Monograph: OLIMEL", Jun. 26, 2018 (Jun. 26, 2018), pp. 1-53, XP055839541, Retrieved from the Internet: URL:https://www.baxter.ca/sites/g/files/ebysai1431/files/2018-11/OLIMEL_EN.pdf [retrieved on Sep. 9, 2021].

Cook S. I. et al: "Revew article: short chain fatty acids in health and disease", Alimentary Pharmacology & Therapeutics, Blackwell Scientific Publications LTD., Cambridge, GB, vol. 12, No. 6, Jun. 1, 1998 (Jun. 1, 1998), pp. 499-507, XP002557049,ISSN: 0269-2813, DOI: 10.1046/J.1365-2036.1998.00337.X [retrieved on Dec. 25, 2001].

International Preliminary Report on Patentability for App. No. PCT/US2021/034497 dated Sep. 15, 2022 (28 pages).

Written Opinion of the International Preliminary Examining Authority for PCT/US2021/034497 dated May 4, 2022 (9 pages).

* cited by examiner

PARENTERAL NUTRITION FORMULATION

TECHNICAL FIELD

The disclosure is directed to parenteral nutrition formulations, including ready-to-use parenteral nutrition formulations which are reconstituted from multi-chamber containers and amino acid formulations. More particularly, the present disclosure is directed to formulations comprising butyrate derivatives, specifically arginine butyrate, for use with pediatric or adult patients. The disclosure further provides for methods of reducing or preventing systemic and local inflammation of patients receiving parenteral nutrition, and methods of maintaining or ameliorating their systemic immunity and local immunity, as well as the patients' gut barrier functions.

BACKGROUND AND DESCRIPTION OF THE RELATED ART

Parenteral nutrition (PN) prevents progressive malnutrition and provides lifesaving therapy for many patients with gastrointestinal disorders. However, PN seems to be associated with an increased incidence of infection and inflammation, both local and systemic, in critically ill patients on prolonged parenteral nutrition, where no oral or enteral uptake of any nutrition is possible. Studies have also suggested that impairment of intestinal barrier function might be at least partially responsible (Fukatsu and Kudsk, Surg Clin North Am. 2011; 91(4): 755-770). Accordingly, the intestinal tract's barrier ("intestinal barrier", "gut barrier" or simply "barrier", as interchangeably used herein), local and systemic inflammation and local and systemic (non specific) immunity have been the object of investigation for many years.

The intestinal tract is lined by a single layer of columnar epithelial cells that forms said gut barrier which allows for selective absorption of nutrients, while restricting access to pathogens and food-borne antigens. Precise regulation of epithelial barrier function is therefore required for maintaining mucosal homeostasis and depends, in part, on barrier-forming elements within the epithelium and a balance between pro- and anti-inflammatory factors in the mucosa. Pathologic states, such as inflammatory bowel disease, are associated with a leaky epithelial barrier, resulting in excessive exposure to microbial antigens, recruitment of leukocytes, release of soluble mediators, and ultimately mucosal damage. An inflammatory microenvironment (herein referred to as "local inflammation") affects epithelial barrier properties and mucosal homeostasis by altering the structure and function of epithelial intercellular junctions through direct and indirect mechanisms (Luissint et al., Inflammation and the Intestinal Barrier: Leukocyte-Epithelial Cell Interactions, Cell Junction Remodeling, and Mucosal Repair. *Gastroenterology* 2016; 151(4):616-632).

Another important aspect of the defense built up by the gut relates to the immune system. Notably, the mucosal immune system provides for about 50%-60% of the body's total immunity, producing about 7% of the antibody made by the human body. For example, it produces specific antibodies against intraluminal bacteria in the form of secretory IgA (sIgA), which does not function through inflammation, but rather through adhesion and bacterial exclusion. In the context of the present invention, this is referred to as the "local immunity" of the gut. The protective role of secretory IgA has generally been evaluated in the context of mucosal infections, where it was shown that IgA acts as a first line of defense by preventing attachment and limiting the access of microorganisms to or beneath the epithelium, a process known as immune exclusion. However, IgA also seems to play a crucial role in maintaining the complex interplay between commensals, epithelium, and immune system (Kato et al. Immunological Reviews 2014; 260: 76-75).

While short pauses in oral intake result in minimal alterations in the mucosa/microbial interface, critical illness, with its attendant acidosis, prolonged GI tract starvation, exogenous antibiotics, and breakdown in mucosal defenses may render the host increasingly vulnerable to bacterial challenge. Therefore, a lot of work has already been done to evaluate new chemical entities and their potential role in the development of improved parenteral nutrition formulations which avoid or reduce the effects of long-term PN on the gut as described above, wherein the expression "long-term PN", as used herein, refers to total parenteral nutrition for more than 7, especially more than 10 days and receive from about 95%-100% of their energy needs from parenteral nutrition, and wherein "total parenteral nutrition" (TPN) means that parenteral nutrition is the only source of nutrition the patient is receiving.

It is known also that the route of nutrition affects the inflammatory response generated by both the innate and the adaptive immunity. It was found that enterally fed animals do have increased levels of intestinal IgA, which may serve to neutralize bacteria within the lumen. As mentioned above, gut starvation with parenteral feeding did not increase intestinal (or lung) IgA, denoting a lack in both innate and acquired mucosal immunity.

The above described issues are relevant for all patients receiving PN, including pediatric and adult patients. For example, pre-term infants, due to transient gut immaturity, often require parenteral nutrition for their first few weeks of life. Children suffering from intestinal failure (IF) may even require long-term parenteral nutrition. In addition to the gastrointestinal disorders associated with long-term PN, providing enough protein and energy to sustain their growth and neurodevelopment is a challenge. It could be shown in the past that early parenteral nutrition (PN), including >2.5 g/kg/d of amino acids and at least 40 kcal/kg/d of energy from the first day of life, has been shown to provide sufficient nutritional intakes for reducing nutritional deficits and the incidence of postnatal growth restriction in preterm infants (Rigo and Senterre, The Journal of Nutrition 143 (12), 2913, 2066S-2070S).

Accordingly, it is highly relevant to understand how parenteral nutrition influences the intestinal barrier function, immune cells and inflammatory mediators, and how the composition of a TPN formulation is able to reduce negative effects on the barrier function, local and systemic immunity and local and systemic inflammation. In doing so, also key structural components of the intestinal barrier, specifically the luminal structures termed villi and crypts which are typical for the small intestine, are investigated. Especially short-chain fatty acids have been investigated for their ability to influence gut barrier function, and, to some extent, also on the production of IgA.

Short-chain fatty acids (SCFA) are abundant intraluminal solutes in the large intestine and are the primary energy source for the colonic epithelium. SCFAs are produced by anaerobic fermentation of undigested complex carbohydrates, with acetate, propionate, and butyrate being the most abundant of the SCFAs. Physiologic and clinical studies have shown that SFCAs in general and specifically butyric acid may have trophic effects on both the small and large intestines which may be useful for the prevention and treatment of several acute and chronic conditions, and that IV administration of SCFAs ameliorated mucosal atrophy, and butyric acid-supplemented PN (Bu-PN) both increased intestinal mucosal protein synthesis and stimulated the growth of jejunal and ileal cells in an intestinal resection model (Murakoshi et al., *Journal of Parenteral and Enteral Nutrition* 2011; 35(4): 465-472). It was found that PN supplemented with butyric acid moderately, but significantly, restored PP (Peyer's patches) lymphocyte numbers, as well as intestinal and bronchoalveolar IgA levels, as compared with standard PN. Villous height and crypt depth in the small intestine were significantly decreased in the standard PN group versus the control group, however Bu-PN seemed to restore intestinal morphology.

Another study compared the effects of sodium acetate, sodium propionate and sodium butyrate on rats, where it was found that both intercaecal and intravenous infusion of said SCFA reduced mucosal atrophy (Koruda et al, *Am J Clin Nutr* 1990; 51:685-689).

Pratt et al., Short-Chain Fatty Acid-Supplemented Total Parenteral Nutrition Improves Nonspecific Immunity After Intestinal Resection in Rats. *Journal of Parenteral and Enteral Nutrition* 1996; 20(4):264-271, contemplate that the short-chain fatty acids sodium acetate, sodium propionate and sodium butyrate improve components of nonspecific immune responses and that they may be beneficial in reducing certain aspects of TPN associated immunosuppression after major surgery.

Tappenden et al., Short-Chain Fatty Acid-Supplemented Total Parenteral Nutrition Enhances Functional Adaptation to Intestinal Resection in Rats. *Gastroenterology* 1997; 112:792-802, also describe that Intravenous SCFAs facilitate intestinal adaptation after resection by increasing basolateral intestinal nutrient transport, and that the addition of SCFAs to current TPN formulations may be warranted to improve functional characteristics of the gastrointestinal tract. Also, in this study, sodium acetate, sodium propionate and sodium butyrate were used in the nutrient solutions.

Milo et al., Effects of Short-Chain Fatty Acid-Supplemented Total Parenteral Nutrition on Intestinal Pro-Inflammatory Cytokine Abundance. *Digestive Diseases and Sciences* 2002; 47:2049-2055, discuss that the short-chain fatty acids acetate, propionate and butyrate beneficially increase small intestinal abundance of IL-1β and IL-6 during total parenteral nutrition administration, while not affecting systemic production of these cytokines or intestinal inflammation.

Bartholome et al., Supplementation of Total Parenteral Nutrition With Butyrate Acutely Increases Structural Aspects of Intestinal Adaptation After an 80% Jejunoileal Resection in Neonatal Piglets. *Journal of Parenteral and Enteral Nutrition* 2004; 28(4):210-223 state that administration of TPN supplemented with SCFA (acetic acid, propionic acid and n-butyric acid), or butyrate alone, enhances structural indices of intestinal adaptation in the neonatal piglet after massive small bowel resection by increasing proliferation and decreasing apoptosis.

Jirsova et al., The Effect of Butyrate-Supplemented Parenteral Nutrition on Intestinal Defence Mechanisms and the Parenteral Nutrition-Induced Shift in the Gut Microbiota in the Rat Model. *BioMed Research International* 2019; 2019: 1-14, came to the conclusion that in summary, these findings support the hypothesis that butyrate alleviates the detrimental effect of PN on intestinal permeability via the stimulation of tight junction protein expression.

U.S. Pat. No. 5,919,822 A discloses a method for the use of short chain fatty acids in the form of the free fatty acid, triglyceride, diglyceride, monoglyceride, phospholipid or cholesterol ester in lipids for parenteral or enteral nutrition for the maintenance of gastrointestinal integrity and function of a patient whose gut bacteria flora is jeopardized. Free fatty acids mentioned include acetic acid, propionic acid, butyric acid and caproic acid. It is mentioned there that the composition may support disease resistance and immune competence.

U.S. Pat. No. 7,947,303 B2 discloses the use of butyrate, specifically tributyrin, in enteral formulations for improving digestion and absorption in the intestine and for improving the immune status of a patient.

WO 95/11699 A1 describes certain butyric acid derivatives with the treatment of different diseases. For example, it is suggested to use physiologically stable and safe compounds comprising butyric acid salts, butyric acid derivatives and combinations thereof for the treatment or prophylaxis of gastrointestinal disorders including colitis, inflammatory bowel disease, Crohn's disease, and ulcerative colitis. Specifically, it is proposed to administer such compositions by oral or enema formulations, or by rectal irrigation to maximize their contact with and effectiveness on the gastrointestinal system. Arginine butyrate is also generally mentioned, even though not as a component of a parenteral nutrition formulation and not in connection with any of the above conditions of the gut.

US 2010/222271 A1 describes formulations for enteral administration comprising protein, polyunsaturated fatty acids, short-chain fatty acids and glutamine, wherein the short-chain fatty acid is butyrate and wherein the formulation may further comprise arginine. It further discloses a method for promoting gastrointestinal health by enterally administering such formulation to a patient.

WO 2019/211605 A1 discloses parenteral nutrition formulations for neonates, wherein the formulations comprise greater than 12% w/v arginine, and their use in the treatment of hypoargininaemia, hyperammonemia, negative nitrogen balance and the prevention of weight loss.

Accordingly, the beneficial effects of SCFA, especially butyric acid derivatives, on gut health are well documented. Studies so far have mostly focused on administering sodium butyrate and, to some extent, also on tributyrin. Sodium butyrate especially is a less than ideal candidate for a PN formulation as the sodium load is inevitably increased to the detriment of the patient. Tributyrin, on the other hand, can be associated only with a lipid emulsion for parenteral nutrition, which may not always be the formulation of choice, especially in cases where peripheral administration is preferred or indicated, such as in very young infants. Currently, no such TPN product comprising a butyric acid derivative is available. Accordingly, there is a need to provide a parenteral nutrition formulation comprising a butyric acid derivative which is able to maintain or improve intestinal barrier functionality, reduces inflammatory events locally and preferably also systemically, and which can maintain or improve local and preferably also systemic immunity, and which at the same time is stable and safe for central or peripheral administration to adults and especially also to infants.

Arginine butyrate (L-arginine, butanoate (3:4)), the butyric acid salt of the amino acid arginine, has been described in some detail in the prior art. However, it has not been contemplated in connection with intestinal diseases such as discussed above and has not been considered as a supplement or active component of a parenteral nutrition formulation. Vianello S, Yu H, Voisin V, et al. Arginine butyrate: a therapeutic candidate for Duchenne muscular dystrophy. FASEB J. 2013; 27(6):2256-2269, have discussed arginine butyrate (AB) as a potential drug to treat Duchenne muscular dystrophy, as it combines two pharmacological activities: nitric oxide pathway activation, and histone deacetylase inhibition. Here, arginine was provided as an aqueous solution, wherein arginine was prepared in water and n-butyric acid was added to provide a 26% solution (1 M arginine/1 M butyrate, pH 7) for continuous-chronic injections, and a 12.5% solution (0.76 M arginine/1 M butyrate, pH 5.5) for intermittent injections.

The prior art also mentions that in EBV-related lymphomas, arginine butyrate induces EBV thymidine kinase transcription and may act synergistically with the antiviral agent ganciclovir to inhibit cell proliferation and decrease cell viability. In addition, the butyrate moiety inhibits histone deacetylase, which results in hyperacetylation of histones H3 and H4. Acetylated histones have a reduced affinity for chromatin; this reduced histone-chromatin affinity may allow chromosomal unfolding, potentially enhancing the expression of genes related to tumor cell growth arrest and apoptosis.

McMahon et al., A randomized phase II trial of Arginine Butyrate with standard local therapy in refractory sickle cell leg ulcers. bjh 2010; 151(5):516-524, describe the use of arginine butyrate for the treatment of refractory sickle cell leg ulcers.

It was now found that arginine butyrate can be stably and safely formulated into parenteral nutrition compositions, such as, for example, into amino acid formulations or multi-chamber bags comprising amino acid formulations, carbohydrate formulations and optionally also lipid formulations, where it was found that arginine butyrate can safely and stably administered after reconstitution.

SUMMARY OF THE INVENTION

The inventors have now found that arginine butyrate can improve the intestinal health of parenteral nutrition patients, such as, for example, maintaining or ameliorating local immunity, reducing local inflammation and maintaining or improving intestinal barrier function. It was found that arginine butyrate is surprisingly superior to the butyric acid derivates known as being beneficial for gut health, specifically sodium butyrate and tributyrin. Arginine butyrate (AB) was found to be especially effective in reducing local inflammation as well as increasing local immunity. First results also indicate that AB can also reduce systemic inflammation and increase systemic immunity. It further improves intestinal barrier properties and cellular architecture. At the same time, arginine butyrate was found to be stable and safe when formulated, for example, into an amino acid formulation for parenteral nutrition, and is thus accessible also for patients requiring peripheral administration of a parenteral nutrition product.

In light of the disclosure herein, and without limiting the scope of the invention in any way, in a first aspect of the present invention, which may be combined with any other aspect listed herein unless specified otherwise, a multi-chamber container (MCB) for parenteral administration comprising a carbohydrate formulation present in a first chamber and an amino acid formulation present in a second chamber, wherein at least the first or the second chamber comprises arginine butyrate.

According to a second aspect of the present invention, the multi-chamber container additionally comprises a lipid formulation which present in a third chamber and wherein at least the first, the second chamber or the third chamber of the MCB comprises arginine butyrate.

According to a third aspect of the present invention, the multi-chamber container comprises arginine butyrate in a concentration of from 1 mmol to 300 mmol per liter of reconstituted formulation for administration to a patient in need.

According to a fourth aspect of the present invention, the arginine butyrate is present in the amino acid chamber of the multi-chamber container.

According to a fifth aspect of the present invention, the amino acid formulation of the MCB comprises an aqueous solution of one or more amino acids, dipeptides and/or oligopeptides, and optionally one or more electrolytes selected from the group of electrolytes comprising sodium, potassium, magnesium, calcium, phosphate compounds, and contains multivalent anions of organic acids consisting of malate, citrate, acetate, lactate, gluconate, glucoheptonate, glucono-glucoheptonate, glucose-phosphate or inorganic acids consisting of sulfate, chloride.

According to a sixth aspect of the present invention, the amino acid formulation comprises about 1 g to 30 g of amino acids per 100 mL of the amino acid formulation.

According to a seventh aspect of the present invention, the arginine butyrate is present in the carbohydrate formulation of a multi-chamber container. Alternatively, arginine butyrate is present, in a concentration of from 1 mmol to 300 mmol per liter, in a carbohydrate formulation for parenteral administration, wherein the carbohydrate formulation is not a component of a MCB.

According to an eighth aspect of the present invention, the carbohydrate formulation comprises from 1 g to 100 g of glucose and/or maltose and/or trehalose per 100 mL of carbohydrate formulation, and optionally one or more electrolytes selected from the group of electrolytes consisting of sodium, potassium, magnesium, calcium, phosphate or glycerophosphate.

According to a ninth aspect of the present invention, the arginine butyrate is present in the lipid formulation of the third chamber. Alternatively, arginine butyrate is present, in a concentration of from 1 mmol to 300 mmol per liter, in a lipid formulation for parenteral administration, wherein the lipid formulation is not a component of a MCB.

According to a tenth aspect of the present invention, the lipid formulation comprises an aqueous phase and oil phase in an amount of from 1 g to 40 g of oil per 100 ml of lipid formulation.

According to an eleventh aspect of the present invention, the lipid formulation comprises at least one pharmaceutically acceptable antioxidant selected from the group consisting of alpha-tocopherol, beta-tocopherol, gamma-tocopherol, delta-tocopherol, tocotrienols, and ascorbic acid. Preferably, it comprises alpha-tocopherol.

According to a twelfth aspect of the present invention, the oil phase of the lipid formulation comprises one or more oils selected from the group consisting of olive oil, soybean oil, safflower oil, coconut oil, fish oil, fish oil extract, krill oil, medium-chain triglycerides (MCTs), algae oil, fungi oil, corn oil, sunflower oil, palm kernel oil, and rapeseed oil, preferably one or more oils selected from the group consisting of olive oil, soybean oil, fish oil, fish oil extract, MCTs, algae oil and fungi oil.

According to a thirteenth aspect of the present invention, at least one of the first chamber, the second chamber and the third chamber of the multi-chamber container further comprise vitamins and/or trace elements.

According to a fourteenth aspect of the present invention, the multi-chamber container comprises at least one further chamber containing a vitamin and/or trace element formulation in addition to first, second and/or third chamber, e.g. four, five or six chambers.

According to a fifteenth aspect of the present invention, arginine butyrate is present in a concentration of from 1 mmol to 300 mmol per liter of reconstituted multi-chamber container, from 5 mmol to 300 mmol per liter of reconstituted multi-chamber container, from 1 mmol to 250 mmol per liter of reconstituted multi-chamber container, from 5 mmol to 125 mmol per liter of reconstituted multi-chamber container, from 5 mmol to 75 mmol per liter of reconstituted multi-chamber container, or from 5 mmol to 50 mmol per liter of reconstituted multi-chamber container.

According to a sixteenth aspect of the present invention, the lipid formulation in the third chamber of a MCB comprises tributyrin in a concentration of from 1 mmol to 300 mmol per liter of reconstituted multi-chamber container, wherein the total concentration of equivalent butyric acid does not exceed 301 mmol per liter of the formulation reconstituted from multi-chamber container.

According to a seventeenth aspect of the present invention, the pH of the formulation reconstituted from the multi-chamber container is from 4.5 to 8.0.

According to an eighteenth and further aspect of the present invention, an amino acid formulation for parenteral administration is provided, wherein the amino acid formulation comprises arginine butyrate in a concentration of from 1 mmol to 300 mmol per liter of the amino acid formulation.

According to a nineteenth aspect of the present invention, the arginine butyrate is present in the said amino acid formulation in a concentration of from 1 mmol to 300 mmol per liter of the amino acid formulation, from 5 mmol to 300 mmol per liter of the amino acid formulation, from 1 mmol to 250 mmol per liter of the amino acid formulation, from 5 mmol to 125 mmol per liter of the amino acid formulation, from 5 mmol to 75 mmol per liter of the amino acid formulation, or from 5 mmol to 50 mmol per liter of the amino acid formulation.

According to a twentieth aspect of the present invention, the amino acid formulation comprises an aqueous solution of one or more amino acids selected from the group consisting of alanine (Ala), arginine (Arg), aspartic acid (Asp), glutamic acid (Glu), glutamine (Gln), glycine (Gly), histidine (His), leucine (Leu), isoleucine (Ile), lysine (Lys), methionine (Met), phenylalanine (Phe), proline (Pro), serine (Ser), threonine (Thr), tryptophan (Trp), tyrosine (Tyr), valine (Val), cysteine (Cys), ornithine (Orn), Acetyl-Tyrosine (Ac-Tyr), Acetyl-cysteine (Ac-Cys), taurine and asparagine (Asn); and optionally further comprises one or more electrolytes selected from the group consisting of sodium, potassium, magnesium, calcium, phosphate and glycerophosphate.

According to a twenty-first aspect of the present invention, the amino acid formulation comprises one or more oligopeptides consisting of at least three amino acids and/or dipeptides selected from the group consisting of Alanyl-glutamine (Ala-Gln), Glycyl-glutamine (Gly-Gln), Alanyl-Tyrosine (Ala-Tyr) and glycyl-tyrosine (Gly-Tyr).

According to a twenty-third aspect of the present invention, the amino acid formulation comprises one or more anions of organic acids selected from the group consisting of malate, citrate, acetate, lactate, gluconate, glucoheptonate, glucono-glucoheptonate, glucose-phosphate, and/or an inorganic acid selected from sulfate and chloride.

According to a twenty-fourth aspect of the present invention, the amino acid formulation comprises about 1 g to 30 g of amino acids per 100 mL of the amino acid formulation.

According to a twenty-fifth aspect of the present invention, the amino acid formulation comprises from 20 mg to 25 g per liter of a choline compound selected from the group consisting of choline chloride, choline bitartrate, choline citrate, choline gluconate, choline malate, choline cytidine diphosphate (CDP) salt and glycerophosphocholine (GPC).

According to a twenty-sixth aspect of the present invention, the amino acid formulation further comprises vitamins and/or trace elements.

According to yet another and twenty-seventh aspect of the present invention, compositions reconstituted from multi-chamber container or amino acid formulations according to the invention are provided for parenteral administration to a patient who requires parenteral nutrition when oral and enteral nutrition is not possible, insufficient or contraindicated.

According to a twenty-eighth aspect of the present invention, the composition for parenteral administration is pro critically ill patient tive compositions are configured respectively.

According to a twenty-ninth aspect of the present invention, the composition for parenteral administration is provided to a patient comprising or selected from the group consisting of an intensive care patient, a critically ill patient on short-term parenteral nutrition who is covering 95-100% of the energy needs from parenteral nutrition, a patient suffering from sepsis or septic shock, a short bowel patient, an intestinal failure patient, a metabolically stressed patient, an immunodeficient patient, a cancer patient, a cachexia patient, a malnourished patient, or a patient suffering from or being at risk of developing reduced gut barrier, hyperglycemia and/or hypertriglyceridemia, a critically ill patient for whom enteral nutrition is contraindicated, surgical/postoperative patients with sustained ileus or sustained nothing by mouth (NPO) status, patients with entero-cutaneous fistulas, preterm infants, extreme short bowel patients and/or other home parenteral nutrition (HPN) patients who are covering 95-100% of their energy needs from parenteral nutrition. The compositions are especially beneficial, for example, for intensive care patients, critically ill patients (e.g., on short-term parenteral nutrition who is covering 95-100% of the energy needs from parenteral nutrition, a patient suffering from sepsis or septic shock or for whom enteral nutrition is contraindicated), a short bowel patient, an intestinal failure patient.

According to a thirstiest aspect of the present invention, the composition for parenteral administration is provided to a patient who suffers from or is at risk of developing systemic inflammation and/or local inflammation in the gut.

According to a thirty-first aspect of the present invention, the composition for parenteral administration is provided for sustaining or improving local immunity in the gut and/or lung of a patient.

According to yet another and thirty-second aspect of the present invention, a method of treating patients are provided who require parenteral nutrition when oral and enteral nutrition is not possible, insufficient or contraindicated, and wherein said patients are treated with a composition reconstituted from a multi-chamber container or an amino acid formulation according to the invention.

According to a thirty-third aspect of the present invention, a method of treating a pediatric or an adult patient is provided.

According to a thirty-fourth aspect of the present invention, a method of treating a patient comprising or selected from the group consisting of an intensive care patient, a critically ill patient on short-term parenteral nutrition who is covering 95-100% of the energy needs from parenteral nutrition, a patient suffering from sepsis or septic shock, a short bowel patient, an intestinal failure patient, a metabolically stressed patient, an immunodeficient patient, a cancer patient, a cachexia patient, a malnourished patient and/or a patient suffering from or being at risk of developing a reduced gut barrier, hyperglycemia and/or hypertriglyceridemia are provided, a critically ill patient for whom enteral nutrition is contraindicated, surgical/post-operative patients with sustained ileus or sustained nothing by mouth (NPO) status, patients with entero-cutaneous fistulas, preterm infants, extreme short bowel patients and/or other home parenteral nutrition (HPN) patients who are covering 95-100% of their energy needs from parenteral nutrition.

According to a thirty-fourth aspect of the present invention, a method of treating a patient is provided to a patient who suffers from systemic inflammation and/or local inflammation in the gut.

According to a thirty-fifth aspect of the present invention, the method of treating a patient is provided for sustaining or improving local immunity in the gut and/or lung.

According to a thirty-sixth aspect of the present invention, the method of treating a patient comprises administering a composition according to the invention so as to arrive at an arginine butyrate dose of from 5 mg/kg/day to 10 g/kg/day.

According to a thirty-seventh aspect of the present invention, the method of treating a patient comprises administering a composition according to the invention so as to arrive at an arginine butyrate dose of from 5 mg/kg/day to 5 g/kg/day.

Additional features and advantages of the disclosed formulations are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not necessarily have to have all of the advantages listed herein. Moreover, it should be noted that the language used in the specification has been principally selected for readability and instructional purposes, and not to limit the scope of the inventive subject matter.

BRIEF DESCRIPTION OF THE DRAWINGS

Understanding that figures depict only certain embodiments of the invention and are not to be considered to be limiting the scope of the present disclosure, the present disclosure is described and explained with additional specificity and detail through the use of the accompanying figures.

FIG. 14A refers to the Unconditioned Stimulus (US-CS) response time over fife days of the study, FIG. 14B refers to the Conditioned Stimulus (CS) response time over five days of the study. No significant difference in the cognitive function could be observed between the Groups.

DETAILED DESCRIPTION OF THE INVENTION

Figure 1:
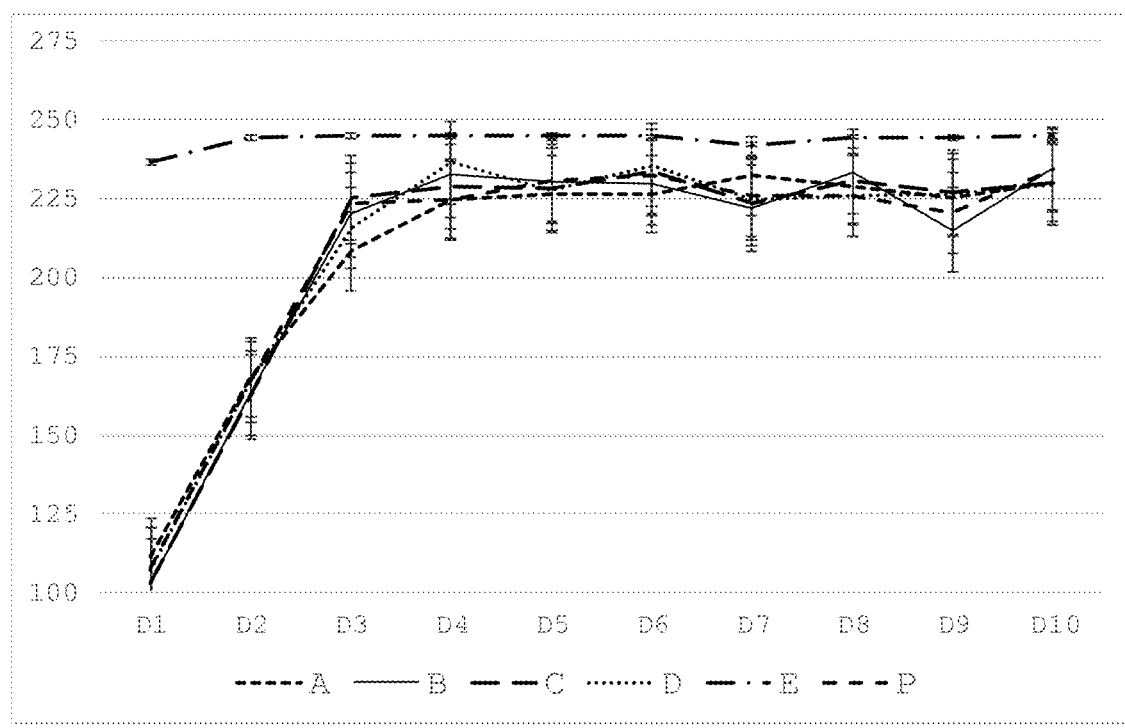
FIG. 1 shows the average energy delivered to piglets in Groups A, B, C, D, E or P (see Table 4) in kcal/kg body weight/day over 10 days (D1 through D10). Group E refers to the piglets which were fed with milk replacer ad libitum. Group P refers to the group on standard parenteral nutrition (S-PN), whereas Groups A, B, C and D received SCFA-PN, i.e. parenteral nutrition wherein the composition administered was supplemented with tributyrin at 10 mmol/L (Group A) or 30 mmol/L (Group B), arginine butyrate at 10 mmol/L (Group C) and 1,2 dipalmitoyl 3-butyryl glycerol at 10 mmol/L (Group D). Energy uptake was comparable for all piglets on S-PN or SCFA-PN.

Certain embodiments described herein relate generally to the field of parenteral nutrition. More particularly, some embodiments described herein relate to amino acid or carbohydrate formulations for parenteral administration, wherein the amino acid formulation comprises arginine butyrate. Related embodiments described herein relate to multi-chamber containers for parenteral administration, wherein the containers comprise a carbohydrate formulation in a first chamber, an amino acid formulation in a second chamber, and optionally a lipid formulation in a third chamber, and wherein arginine butyrate is contained in either of the said chambers.

Accordingly, medical products for parenteral nutrition are provided which comprise arginine butyrate in a concentration of from 1 to 300 mmol per liter of reconstituted formulation. For example, such formulations are reconstituted from a multi-chamber container. PN products are often provided in 3-chamber bags, side-by-side, wherein the lipids, carbohydrates and amino acids can be admixed before administration by breaking non-permanent peel seals between the respective chambers. Electrolytes can also be contained in the nutrition solutions. Trace elements and vitamins are often added to the parenteral nutrition solutions before administration to the patient or are administered separately from the parenteral nutrition. The lipids are a concentrated source of energy which are provided as oil-in-water emulsions. However, lipids can be infused separately, especially when patients have a high protein and/or minimal fluid need and do not have increased energy needs.

The expression "pediatric" as used herein refers to neonates, including premature (pre-term), full term, and post-mature neonates of up to one month of age; infants of between one month and one year of age; children of between one and up to 12 years of age, and adolescents of between 13 and up to 21 years of age. The formulations according to the invention are specifically suitable for neonates, including pre-term, full-term and post-mature neonates. The formulations are especially suitable for pre-term neonates, who may have a birthweight of below 2500 g, of below 2000 g, of below 1800 g, of below 1500 g, of below 1200 g, of below 1100 g, or even of below 1000 g.

The expression "short-chain fatty acid" or "SCFA" as used herein refers to fatty acids with fewer than six carbon atoms. Table 1 provides for a list of the short-chain fatty acids, their common and systemic names as well as their formulas.

TABLE 1

List of short-chain fatty acids and their respective names and formulas

| Lipid Number | Name | | Salt Name | | Formula | |
|---|---|---|---|---|---|---|
| | Common | Systematic | Common | Systematic | Molecular | Structural |
| C1:0 | Formic acid | Methanoic acid | Formate | Methanoate | $CH_2O_2$ | HCOOH |
| C2:0 | Acetic acid | Ethanoic acid | Acetate | Ethanoate | $C_2H_4O_2$ | $CH_3COOH$ |
| C3:0 | Propionic acid | Propanoic acid | Propionate | Propanoate | $C_3H_6O_2$ | $CH_3CH_2COOH$ |
| C4:0 | Butyric acid | Butanoic acid | Butyrate | Butanoate | $C_4H_8O_2$ | $CH_3(CH_2)_2COOH$ |
| C4:0 | Isobutyric acid | 2-Methylpropanoic acid | Isobutyrate | 2-Methylpropanoate | $C_4H_8O_2$ | $(CH_3)_2CHCOOH$ |
| C5:0 | Valeric acid | Pentanoic acid | Valerate | Pentanoate | $C_5H_{10}O_2$ | $CH_3(CH_2)_3COOH$ |
| C5:0 | Isovaleric acid | 3-Methylbutanoic acid | Isovalerate | 3-Methylbutanoate | $C_5H_{10}O_2$ | $(CH_3)_2CHCH_2COOH$ |

Accordingly, it is one aspect of the present invention to provide for a product for central or peripheral administration which is preferably comprised of an amino acid formulation, which may additionally also comprise electrolytes, and a carbohydrate formulation, which preferably comprises glucose and optionally calcium, and wherein arginine butyrate is comprised in the amino acid chamber or the carbohydrate chamber or in both chambers of the product. According to another aspect of the invention, the product does not comprise a lipid formulation and therefore consists of a two-chamber container. According to one embodiment, the chambers are designed to contain the formulations which upon reconstitution result in a volume of from 0.8 to 2.2 L. Preferably, the resulting volume after reconstitution is from 1.0 to 2.0 L, for example 1.0, 1.5 or 2.0 L. Obviously, the volumes of the first and the second chamber can vary so as to result in the above disclosed final reconstituted volumes. However, a lipid formulation can be added before administration or can be provided separately from the administration of the medical product according to the invention.

According to another aspect of the invention, such lipid formulation can be combined with the amino acid and carbohydrate formulation in a product (then comprising three chambers). In this case, the arginine butyrate can be present in either of the three chambers, that is in the amino acid chamber, the carbohydrate chamber or the lipid chamber. Preferably, the arginine butyrate is present in the amino acid chamber. Various alternatives and embodiments of the invention are described in further detail below.

Short-chain fatty acids are liquid at room temperature and generally have a pungent or rancid odor, which makes the difficult to use in parenteral nutrition solutions. Their alkali metal salts are hydrolyzed in aqueous solutions. They are described in some detail in Schönfeld and Wojtczak, Short- and medium-chain fatty acids in energy metabolism: the cellular perspective. *J Lipid Res* 2016; 75(6):943-954. According to the invention, the expression "short-chain fatty acids" encompasses glycerol esters of the above SCFA, including, but not limited to, tributyrin.

The expression "parenteral nutrition" (PN) as used herein refers to the intravenous administration of nutritional components, which may include protein, carbohydrate, fat, minerals and electrolytes, vitamins and trace elements, to patients who cannot eat or absorb enough food through tube (enteral) feeding to maintain good nutrition status. Diseases and conditions where PN is indicated include but are not limited to short bowel syndrome, GI fistulas, bowel obstruction, critically ill patients (e.g., on short-term parenteral nutrition who is covering 95-100% of the energy needs from parenteral nutrition, a patient suffering from sepsis or septic shock), and severe acute pancreatitis. Patients receiving PN include pre-term or newborn babies, infants, children and adults.

The expression "parenteral nutrition solution" as used herein generally refers to a sterile liquid chemical formula suitable for parenteral nutrition and which is given directly into the bloodstream of a patient through an intravenous (IV) catheter. A parenteral nutrition solution provided in, for example, a multi-chamber container is considered a medical product.

The expression "total parenteral nutrition (TPN)" as used herein implies that all macronutrient (carbohydrate, nitrogen and lipid) and micronutrient (vitamins, trace elements and minerals) and fluid requirements of a patient are met by an intravenous nutrient solution and no significant nutrition is obtained from other sources.

The expression "gut" as used herein, refers to the intestine. The expressions are interchangeably used herein. The intestine consists of the small intestine, colon (large intestine) and rectum. The small intestine is divided into the duodenum, jejunum, and ileum.

The expression "reconstitution" as used herein, refers to the mixing of fluids contained in distinct chambers within a multi-chamber bag by opening or breaking one or more non-permanent (peel) seals which separate the chambers and the fluids contained therein. A "reconstituted" fluid thus is a fluid which is obtained by mixing two or more fluids located in different chambers of a multi-chamber bag. Such reconstitution is generally done shortly before administration of the reconstituted fluid to a patient.

The expression "systemic inflammation" as used herein refers to inflammation affecting the entire body rather than a single organ or body part, which is referred to herein as "local inflammation. The expression "inflammation" as used herein refers to the response of body tissues to harmful stimuli, including the production of eicosanoids and cytokines, which are released by injured or infected cells.

The expression "systemic immunity" as used herein refers to the state of a human being having adequate biological defenses to fight infection, disease, or other unwanted biological invasion. "Local immunity" or "regional immunity" as used herein refers to the ability of a body part or organ to fight infection, disease, or other unwanted biological invasion. In the context of the present invention, "local immunity" relates to the ability of the intestine to effectively respond to such infection, disease, or other unwanted biological invasion.

The multi-chamber container (MCB) according to the invention comprises nutritional formulations for parenteral administration to a patient. For example, the container may be in the form of a bag having multiple compartments or chambers. The container includes at least two chambers, but can also include three, four, five or more chambers. Suitable containers, including bags, typically are sterile, non-pyrogenic, single-use, and/or ready-to-use products. The multi-chamber containers are particularly useful for holding a parenteral nutrition product and generally provide a carbohydrate formulation as disclosed herein in the first chamber, an amino acid formulation as disclosed herein in a second chamber, and optionally a lipid formulation as disclosed herein in a third chamber of the container. The multi-chamber containers may also provide a fourth chamber or a fifth chamber which comprise, for example, selected vitamins and/or trace elements which cannot be admixed to the carbohydrate, amino acid or lipid formulation for reasons of stability or because their addition is intended to be optional.

The expression "peripheral parenteral nutrition (PPN)" as used herein refers to the administration of PN solution via a cannula inserted into a peripheral vein. The term "peripheral" refers to superficial veins, most often of the upper extremities. PPN is indicated, for example, for short-term PN, when catheterization of a central vein is contraindicated or impossible, in case of catheter sepsis or bacteremia. In contrast, "central parenteral nutrition" refers to parenteral nutrition (PN) which is given via a central vein. Central access allows for the use of highly concentrated, hypertonic solutions, and are often used for patients requiring PN for more than 2 weeks. Either a temporary central venous catheter (CVC) or long-term CVC, such as a tunneled catheter, an implanted port, or a peripherally inserted central catheter (PICC) can be used. As CVCs can increase catheter-related blood stream infections, peripheral parenteral nutrition (PPN) is used where indicated The multi-chamber container of the invention, such as, for example, a three-chamber bag, may include vertical chambers. Suitable multi-chamber containers are disclosed in U.S. Patent Publication No. 2007/0092579. For example, the multi-chamber container may be configured as a bag that includes two or three adjacent chambers or compartments. If desired, frangible barriers or openable seals (e.g., peel seals or frangible seals) are used to separate the chambers of the multi-chamber container. Multi-chamber containers may also comprise three chambers for accommodating a lipid emulsion, a carbohydrate formulation and an amino acid formulation, and further comprise at least one, in certain embodiments two or three smaller chambers which contain, for example, vitamin formulations and/or trace element formulations. In one specific embodiment, the multi-chamber container of the invention has a first chamber containing the lipid emulsion according to the invention, a second chamber containing an amino acid formulation, a third chamber containing a carbohydrate formulation, a fourth chamber containing a vitamin formulation and a fifth chamber containing a trace element formulation. The openable seals of said multi-chamber containers permit formulations to be separately stored and admixed/reconstituted just prior to administration thereby allowing storage in a single container of formulations which should not be stored as an admixture for an extended period of time. Opening of the seals allows communication between the chambers and mixing of the contents of the respective chambers. The outside seals of the multi-chamber container are strong seals that do not open under the fluid pressure supplied to open the weaker peel seals or frangible seals between the chambers. In some embodiments, the openable seals of the multi-chamber container may be designed to allow for the admixing or reconstitution of only selected chambers of the multi-chamber container, for example, the admixing of the lipid emulsion with the vitamin chamber and the amino acid chamber, if so desired.

The multi-chamber container according to the invention may be provided with instructions explaining a desired order with which to open the peel seals, so that constituent fluids are mixed in a desired order. The unsealing strengths of the two or more peel seals may be varied to promote the opening of the seals in the desired order. For example, the unsealing strength of the peel seal to be opened first may be ⅓ to ½ of the unsealing strength required to open the peel seal to be opened second.

The containers can be made principally of flexible polymeric materials, although the container could include non-polymeric materials such as metal foils without departing from the disclosure. Numerous polymeric films have been developed for use in containers. Suitable films may be of a monolayer structure or a multiple layer structure. The monolayer structure can be made from a single polymer, or from a polymer blend. The multiple layer structures can include layers such as a solution contact layer, a scratch resistant layer, a barrier layer for preventing permeation of gas (such as carbon dioxide, oxygen or water vapor), tie layers, or other layers. It is also contemplated to use more than one web of film for one or both sidewalls. Appropriate polymeric materials are generally selected from homopolymers and copolymers of polyolefins, polyamides, polyesters, polybutadiene, styrene and hydrocarbon copolymers, polyimides, polyester-polyethers, polyamide-polyethers to name a few. It is preferably to use non-PVC materials for the primary packaging, including the film and the port tubes as well as the twist-off protector. According to one embodiment of the invention, the film of the primary packaging of the medical product of the invention is a four-layer co-extruded film prepared from poly(cyclohexylenedimethylene)cyclohexane dicarboxylate copolymer (PCCE) (outer layer), maleic anhydride modified poly(ethylene vinyl acetate) (tie layer), poly (ethylene vinyl acetate) (EVA) (inside layer), and poly (ethylene-propylene) copolymer (PP/PE) and styrene-ethylene-butylene-styrene block polymer (SEBS) (sealant layer). According to another embodiment, the port tube(s) are polyolefin-based, three layered, co-extruded components which are PVC free. The outer layer is prepared from a blend of PP/PE and SEBS, the middle layer from a blend of SEBS, EVA, PP and PE, and the inner layer from EVA. The middle layer is optional and can basically be replaced with a virtual layer consisting of the same material as the outer layer. According to yet another aspect of the invention, the TOP can be made from a blend of PP, EVA SEBS and optionally comprise a color, such as, for example, Polybatch® Blue. The TOP preferably is PVC-free.

The seal layer for the container of the product of the invention should display bi-modal behavior. What is meant by bi-modal behavior is that the material is capable of forming a permanent seal under one set of sealing or manufacturing conditions and a peelable seal at a second set of sealing or manufacturing conditions. The seal layer can be a homophase polymer, or a matrix-phase polymer system. Suitable homophase polymers include polyolefins and polypropylene, specifically a propylene and ethylene copolymer.

As mentioned above, typical components of a multi-chamber container for providing formulations for parenteral nutrition are amino acid and/or carbohydrate formulations. The carbohydrate formulations provide a supply of calories, typically in the form of glucose. Maltose or trehalose can also be used. Mixtures of glucose with maltose and/or trehalose are also possible. In particular, the carbohydrate formulation provides an amount of carbohydrate sufficient to avoid adverse effects such as hyperglycemia that has been observed in patients receiving parenteral nutrition. Typically, the carbohydrate formulation includes from 1 to 100 grams per 100 ml of glucose, maltose, trehalose or mixtures thereof. In certain embodiments of the invention, the carbohydrate formulation includes from 20 to 50 grams or from 15 to 30 grams of glucose, maltose, trehalose or mixtures thereof per 100 mL of carbohydrate formulation.

According to one embodiment, glucose is contained in in an amount of from 30 to 40 grams per 100 ml of the carbohydrate formulation. According to another embodiment, glucose is contained in in an amount of from 24 to 30 grams per 100 ml of glucose. For example, glucose compositions such as described in U.S. patent application Ser. No. 16/562,014 can be supplemented with arginine butyrate according to the invention.

The carbohydrate formulation may further include a water-soluble form of choline selected from the group consisting of choline chloride, choline bitartrate, choline citrate, choline gluconate, choline malate, choline cytidine diphosphate choline (CDP) salt and glycerophosphocholine. In a preferred embodiment, the water-soluble form of choline is present in a concentration of from 20 mg to 25 g choline equivalent per liter of the reconstituted multi-chamber container, for example, from about 30 mg to 20 g, from about 30 mg to 15 g, from about 30 mg to about 10 g, from about 30 mg to 5 g, from about 30 mg to 1 g, from about 30 mg to 800 mg, from about 100 mg to 1 g, from about 500 mg to 1 g, from about 800 mg to 10 g or from about 1 g to 10 g choline equivalent per liter of the reconstituted multi-chamber container. The carbohydrate formulation may include calcium in a concentration of from 0.1 mmol to 10 mmol. In such case, calcium may be provided in the form of calcium chloride $2.H_2O$ or calcium gluconate.

The amino acid formulation according to the invention can be a component of a multi-chamber container as described before or can be a separate product for parenteral nutrition and administration to a patient in need. The amino acid formulation includes a sterile, aqueous solution of one or more amino acids, dipeptides and/or oligopeptides and optionally one or more electrolytes. If not specifically indicated otherwise, the expression "amino acid" or amino acids" is generically used herein and encompasses amino acids, dipeptides and oligopeptides.

Typically, the amino acid formulation includes from about 1 gram to about 30 grams of amino acids per 100 mL of amino acid formulation, such as from about 3 grams to about 25 grams, from about 4 grams to about 20 grams, from about 5 grams to about 15 grams and from about 5 grams to about 10 grams per 100 mL of amino acid formulation. The amino acid formulation generally includes one or more amino acids selected from the group consisting of alanine (Ala), arginine (Arg), aspartic acid (Asp), glutamic acid (Glu), glutamine (Gln), glycine (Gly), histidine (His), leucine (Leu), isoleucine (Ile), lysine (Lys), methionine (Met), phenylalanine (Phe), proline (Pro), serine (Ser), threonine (Thr), tryptophan (Trp), tyrosine (Tyr), valine (Val), cysteine (Cys), ornithine (Orn), taurine and asparagine (Asn). The amino acid formulations according to the invention can further comprise oligopeptides consisting of at least three amino acids and/or dipeptides selected from the group consisting of Acetyl-cysteine (Ac-Cys), Acetyl-Tyrosine (Ac-Tyr), Alanyl-glutamine (Ala-Gln), Glycyl-glutamine (Gly-Gln), and glycyl-tyrosine (Gly-Tyr). Further, the content of tyrosine can be increased by adding, for example, acetyl-tyrosine (Ac-Tyr).

The amino acid formulation according to the invention may further include electrolytes such as sodium, potassium, calcium, magnesium, and/or phosphate ions and/or anions of organic acids selected from the group consisting of malate, citrate, acetate, lactate, gluconate, glucoheptonate, glucono-glucoheptonate, glucose-phosphate, and/or an inorganic acid selected from sulfate and chloride. For example, the amino acid formulation can include from about 0.1 mmol to about 10 mmol of sodium (e.g., about 3.75 mmol to about 10 mmol of sodium), from about 0.1 mmol to about 10 mmol of potassium (e.g., about 3.75 mmol to about 6.90 mmol of potassium), from about 0.05 mmol to about 1.0 mmol of magnesium (e.g., about 0.05 mmol to about 0.11 mmol and/or about 0.38 mmol to about 0.65 mmol of magnesium), from about 0.1 mmol to about 10 mmol of calcium (e.g., about 1.13 mmol to about 5.10 mmol of calcium), from about 0.1 mmol to about 10 mmol of phosphate (e.g., about 0.94 mmol to about 5.10 mmol of phosphate) and not more than 10 mmol of chloride (e.g., not more than 5.6 mmol of chloride) per 100 mL of amino acid formulation. When calcium and phosphorus are present together in the same heat-sterilized solution, insoluble calcium phosphate precipitation can occur. Using an organic salt of phosphorus such as sodium glycerophosphate $5.H_2O$ or calcium glycerophosphate, calcium and phosphate amounts may be increased without solubility issues and without providing excess sodium or chloride. In the amino acid formulation, sodium may be provided in the form of sodium chloride or sodium acetate, calcium may be provided in the form of calcium chloride 2.H$_2$O or calcium gluconate, magnesium may be provided in the form of magnesium acetate 4.H$_2$O, magnesium sulfate 5.H$_2$O or magnesium chloride, and potassium may be provided in the form of potassium acetate or potassium chloride.

The amino acid formulation may further include a water-soluble form of choline selected from the group consisting of choline chloride, choline bitartrate, choline citrate, choline gluconate, choline malate, choline cytidine diphosphate choline (CDP) salt and glycerophosphocholine. In a preferred embodiment, the water-soluble form of choline is present in a concentration of from 20 mg to 25 g choline equivalent per liter of the reconstituted multi-chamber container, for example, from about 30 mg to 20 g, from about 30 mg to 15 g, from about 30 mg to about 10 g, from about 30 mg to 5 g, from about 30 mg to 1 g, from about 30 mg to 800 mg, from about 100 mg to 1 g, from about 500 mg to 1 g, from about 800 mg to 10 g or from about 1 g to 10 g choline equivalent per liter of the reconstituted multi-chamber container.

The multi-chamber container according to the invention can also comprise a lipid formulation in a third chamber. Such lipid formulation is an emulsion of an oil phase, a water phase, and an emulsifier that makes the two phases miscible. In case of lipid emulsions, which are to be used as an injectable emulsion for parenteral nutrition, the emulsion must be an oil-in-water (o/w) emulsion. This means that the oil must reside in the internal (or dispersed) phase, while water is the external (or continuous) phase, as the emulsion must be miscible with blood. Lipid emulsion as disclosed herein must therefore also be substantially free of any suspended solids. Of course, the lipid emulsions may contain further components, including, but not limited to, antioxidants, pH modifiers, isotonic agents, vitamins, trace elements and various combinations thereof. An overview over lipid emulsions, their composition and use is provided, for example, in Driscoll, Journal of Parenteral and Enteral Nutrition 2017, 41, 125-134. Further information on the use of lipid emulsions in parenteral nutrition of intensive care patients is provided, for example, in Calder et al, Intensive Care Medicine, 2010, 36(5), 735-749.

Typically, the lipid formulation contains from about 1 g to 40 g of oil per 100 ml of lipid formulation. For example, the lipid formulation contains from about 1 g to 35 g, from about 5 g to 35 g, from about 5 g to 30 g, from about 10 g to 30 g, from about 10 g to 25 g, from about 15 g to 20 g, or from about 12 g to 18 g of oil per 100 ml of lipid formulation.

Lipid emulsions contained in one chamber of a multi-chamber according to the invention may contain glycerophosphocholine (GPC) in a concentration of from 0.1 g to 15.0 g per liter. In some embodiments, the GPC concentration in such multi-chamber container may be from 1.0 g to 12 g per liter of lipid emulsion, from 1.0 g to 10.0 g per liter of lipid emulsion, from 2 g to 9.0 g per liter lipid emulsion, from 1.0 g to 5.0 g per liter of lipid emulsion, or from 2.0 g to 4.0 g per liter of lipid emulsion. Lipid emulsion comprising GPC are further described in WO 2019/0232054 A1, which is incorporated herein in its entirety. Other water-soluble forms which can also be added to the lipid emulsion alone or in combination with GPC or each other may be selected from the group consisting of choline chloride, choline bitartrate, choline citrate, choline gluconate, choline malate and choline cytidine diphosphate choline (CDP) salt (e.g., sodium salt, potassium salt, or inner salt). In a preferred embodiment, GPC or choline chloride is present in a concentration of from 0.1 g to 12 g of choline equivalent per liter of lipid emulsion.

The oil phase of the lipid emulsion which can be combined with the amino acid and glucose formulation according to the invention generally includes polyunsaturated fatty acids, such as long-chain polyunsaturated fatty acids, which may be present as the free acid, as an ionized or salt form of the free acid, and/or in ester form. Suitable esters of the polyunsaturated fatty acids/long-chain polyunsaturated fatty acids include, but are not limited to, alkyl esters (e.g., methyl esters, ethyl esters, propyl esters, or combinations thereof) and triglyceride esters. In some cases, the long-chain polyunsaturated fatty acid has a structure R(C=O)OR', wherein R is an alkenyl group having at least 17 carbon atoms, at least 19 carbon atoms, at least 21 carbon atoms, or at least 23 carbon atoms, and R' is absent, H, a counter ion, an alkyl group (e.g., methyl, ethyl, or propyl), or a glyceryl group (e.g., R(C=O)OR' is a monoglyceride, a diglyceride, or a triglyceride). Polyunsaturated fatty acids for use in the lipid formulations disclosed herein include, but are not limited to, linoleic acid (LA), arachidonic acid (ARA), α-linolenic acid (ALA), eicosapentaenoic acid (EPA), docosahexaenoic acid (DHA), stearidonic acid (SDA), γ-linolenic acid (GLA), dihomo-γ-linolenic acid (DPA), and docosapentaenoic acid (DPA), particularly, DHA, ARA, and EPA, each of which may be present in free acid form, ionized or salt form, alkyl ester form, and/or triglyceride form. In some cases, the polyunsaturated fatty acids and/or long-chain fatty acids are present in triglyceride form.

The oil phase and its components can be derived from a single source or different sources (see, for example, Fell et al, Advances in Nutrition, 2015, 6(5), 600-610). Of the plant oils, currently used sources include, but are not limited to, soybean and olive oil as well as safflower oil, corn oil, sunflower oil, rapeseed oil, coconut or palm kernel oil. The oil phase may further comprise medium-chain triglycerides (MCTs). Another source are algae, including microalgae such as *Crypthecodinium cohnii* and *Schizochytrium* sp. Marine oil, generally fish oil or fish oil extract, as used in parenteral lipid emulsions is processed from oily fish primarily found in cold water and including, but not limited to, herring, shad and sardines. However, other marine organisms can be used as an oil source, such as, for example, krill, such as Antarctic krill (*Euphausia superba* Dana). The oil used in a lipid formulation according to the invention can be from one or more of the above sources. Preferred combinations are, for example, a combination of soybean and olive oil, a combination of soybean oil, olive oil, MCTs and fish oil or fish extract, a combination of soybean oil, olive oil, MCTs, fish oil or fish extract and krill oil. Preferably, the lipid formulation according to the invention has a phytosterol content of below 175 mg, 150 mg, 120 mg, preferably below 100 mg and especially preferably below 70 mg phytosterols per 100 g of oil phase. Such lipid formulations and methods to produce them have been described in WO 2019/232044 A1 and WO 2020/007758 A1.

The lipid formulations disclosed herein may further include additional components, such as surfactants (also referred to as emulsifiers), co-surfactants, isotonic agents, pH adjusters, and antioxidants. Generally, surfactants are added to stabilize emulsions by reducing the interfacial tension between the oil phase and the aqueous phase. Surfactants typically include a hydrophobic part and a hydrophilic part, and the amount of surfactant/emulsifier included in the formulations is determined based on the amount that is needed to achieve a desired level of stabilization of the emulsion. Typically, the amount of surfactant in the lipid formulation is about 0.01% to about 3% by weight based on the total weight of the lipid formulation, for example, about 0.01% to about 2.5%, about 0.01% to about 2.3%, about 0.02% to about 2.2%, about 0.02% to about 2.1%, about 0.02% to about 2%, and/or about 0.05% to about 1.8% by weight.

Suitable surfactants and co-surfactants include surfactants that are approved for parenteral use, and include, but are not limited to, phospholipids (e.g., egg phosphatide and soy lecithin), oleate salts, and combinations thereof. Krill oil can also be used as an emulsifier in the lipid emulsion, wherein the lipid emulsion comprises about 0.5 to 2.2 wt % krill oil based on the total weight of the emulsion, and wherein the emulsion is free of egg yolk lecithin (US 2018/0000732 A1). An-other exemplary surfactant is lecithin, including both natural and synthetic lecithin, such as lecithins derived from egg, corn or soybean or mixtures thereof. In some cases, lecithin is included in an amount of about 1.2% based on the total weight of the lipid formulation.

In some cases, the lipid emulsion formulation includes a co-surfactant. Typically, the amount of co-surfactant in the lipid formulation is less than the amount of surfactant, and typically the amount of co-surfactant in the formulation is about 0.001% to about 0.6% by weight based on the total weight of the lipid formulation, for example, about 0.001% to about 0.55%, about 0.001% to about 0.525%, about 0.001% to about 0.5% and/or about 0.05% to about 0.08%. An exemplary co-surfactant is oleate, such as sodium oleate. In some cases, the lipid formulation includes lecithin and oleate as surfactant and co-surfactant, for example, an in amount of 1.2% lecithin and 0.03% oleate. In some cases, sodium oleate is included in an amount of about 0.03% by weight based on the total weight of the lipid formulation.

Isotonic agents can be added to the lipid emulsions to adjust the osmolarity of the lipid emulsion to a desired level, such as a physiologically acceptable level. Suitable isotonic agents include, but are not limited to, glycerol. Typically, the lipid emulsion formulation has an osmolarity of about 180 to about 300 millimols/liter, such as about 190 to about 280 millimols/liter, and/or about 200 to about 250 millimols/liter. In some cases, the lipid emulsion includes an isotonic agent in an amount of about 1% to about 10% by weight based on the total weight of the lipid formulation, such as about 1% to about 5%, about 1% to about 4%, and/or about 2% to about 3%. In some cases, the lipid emulsion formulation includes about 2% to about 3% by weight of glycerol.

pH modifiers can be added to the lipid emulsions to adjust the pH to a desired level, such as a physiologically acceptable pH for parenteral use. Suitable pH modifiers include but are not limited to sodium hydroxide and hydrochloric acid. Typically, the lipid emulsion formulation has a pH of about 6 to about 9, such as about 6.1 to about 8.9, about 6.2 to about 8.8, about 6.3 to about 8.7, about 6.4 to about 8.6, about 6.5 to about 8.5, about 6.6 to about 8.4, about 6.7 to about 8.3, about 6.8 to about 8.2, about 6.9 to about 8.1, about 7 to about 8, about 7.1 to about 7.9, about 7.2 to about 7.8, about 7.3 to about 7.7, about 7.4 to about 7.6, about 7, about 7.5, and/or about 8.

The lipid formulations may further include antioxidants. Suitable antioxidants may be pharmaceutically acceptable antioxidants and include, but are not limited to, tocopherols (e.g., alpha tocopherol, beta tocopherol, gamma tocopherol, delta tocopherol), tocotrienols, ascorbic acid, ascorbyl palmitate, or combinations thereof. In some cases, the lipid emulsion formulation includes an antioxidant in an amount of about 0 to about 300 mg/L, for example, about 10 to about 250 mg/L, about 40 to about 180 mg/L, about 50 to about 120 mg/L, about 75 to about 100 mg/L antioxidant(s), such as, preferably, alpha-tocopherol.

The aqueous (or water) phase of all intravenous formulations, including the amino acid, carbohydrate and lipid emulsions must conform to the pharmacopeial requirements that make it suitable for injection, that is the water must be sterile water for injection.

The reconstituted formulations for parenteral administration from a multi-chamber container according to the invention comprise arginine butyrate in a concentration of from 1 to 300 mmol per liter. Accordingly, depending on the configuration of the multi-chamber container (two, three, four, five or more chambers), and the respective volumes of the chambers, the amount of arginine butyrate to be added to, for example, the amino acid chamber, has to be calculated based on the final volume of reconstituted solution of the multi-chamber container.

The arginine butyrate supplemented amino acid formulation and the arginine butyrate supplemented formulation can be prepared by providing a concentrated solution of arginine butyrate by dissolving the compound in Water for Injection. From that concentrated solution an amount required for generating the desired final concentration is added to the amino acid formulation or carbohydrate formulation, respectively.

For example, arginine butyrate supplemented amino acid formulations can be prepared by filling a cleaned and nitrogen flushed mixing tank with a first batch of water for injection. When the required temperature is reached, amino acids, arginine butyrate, optionally electrolytes and, for example, glacial acetic acid or malic acid, as needed, are added to the tank. Agitation is initiated, and the solution is adjusted to final volume with water for injection. The pH of the solution is measured and if needed adjusted with glacial acetic acid or malic acid to the required pH. The solution is visually checked to ensure it is a clear solution. The dissolved oxygen and the density of the solution are measured.

Arginine butyrate supplemented carbohydrate formulations can be prepared, for example, by filling a cleaned and nitrogen flushed mixing tank with Water for Injection. When the required temperature is reached glucose, trehalose and/or maltose and optionally calcium chloride are added to the tank. Agitation is initiated. The pH of the solution is measured and if needed adjusted for example with hydrochloric acid 25% to the required pH. The solution is visually checked to ensure it is a clear solution. The dissolved oxygen and the density of the solution are measured.

During the filling process, the supplemented amino acid or carbohydrate solutions are filtered online through a 0.45 μm filtration membrane. Fill volume is determined gravimetrically and is periodically checked during the filling process to ensure uniformity across the batch. Additionally, dissolved oxygen is measured on the first filled containers. The containers are then sealed. Each filled and sealed container is placed in an overpouch along with one oxygen absorber. The interior space of the overpouch is flushed with nitrogen to reduce the level of oxygen and the overpouch is heat-sealed. The overpouched bags are placed on sterilizer trays for moist heat sterilization. The product can be terminally sterilized at 121° C. and 2.2 bar using a moist heat sterilization process adapted for the selected sizes/volumes of the containers. For example, a SteamAir Mixture process can be utilized. The exposure time is adapted to the size of the container.

The concentration of arginine butyrate can be varied relatively broadly over the disclosed range. It was found to be stable during production, sterilization and over a shelflife of at least 12 months at 25° C. and 40% relative humidity (RH) in the amino acid formulation (see also Example 1 and Table 5).

For example, arginine butyrate can be present in a concentration of from 1 mmol to 300 mmol per liter of reconstituted multi-chamber container, from 5 mmol to 300 mmol per liter of reconstituted multi-chamber container, from 1 mmol to 250 mmol per liter of reconstituted multi-chamber container, from 5 mmol to 125 mmol per liter of reconstituted multi-chamber container, from 5 mmol to 75 mmol per liter of reconstituted multi-chamber container, or from 5 mmol to 50 mmol per liter of reconstituted multi-chamber container. For example, arginine butyrate can be present in a concentration of 5 mmol/L, 8 mmol/L, 10 mmol/L, 15 mmol/L, 20 mmol/L, 25 mmol/l, 30 mmol/L, 35 mmol/L, 40 mmol/L 45 mmol/L or 50 mmol/L.

Accordingly, arginine butyrate can be present in a concentration of from 1 mmol to 300 mmol per liter of amino acid formulation, from 5 mmol to 300 mmol per liter of amino acid formulation, from 1 mmol to 250 mmol per liter of amino acid formulation, from 5 mmol to 125 mmol per liter of amino acid formulation, from 5 mmol to 75 mmol per liter of amino acid formulation, or from 5 mmol to 50 mmol per liter of amino acid formulation. For example, arginine butyrate can be present in a concentration of 5 mmol/L, 8 mmol/L, 10 mmol/L, 15 mmol/L, 20 mmol/L, 25 mmol/l, 30 mmol/L, 35 mmol/L, 40 mmol/L 45 mmol/L or 50 mmol/L.

According to another aspect of the invention, the lipid chamber of the multi-chamber container according to the invention additionally comprises tributyrin in a concentration of from 1 mmol to 300 mmol per liter of reconstituted multi-chamber container, wherein the total concentration of equivalent butyric acid does not exceed 301 mmol per liter of reconstituted multi-chamber container. In other words, the multi-chamber container according to the invention may comprise arginine butyrate in the amino acid or the carbohydrate formulation (or in both), and the lipid formulation comprises tributyrin. The final concentration of equivalent butyric acid should, however, not exceed the 301 mmol/L of reconstituted multi-chamber container. Accordingly, care should be taken to adjust the respective concentrations respectively, keeping in mind that one molecule tributyrin provides for three equivalents of butyric acid. Methods of preparing tributyrin containing lipid formulations are known in the art and have been described, for example, in U.S. Pat. No. 5,919,822 A.

According to yet another aspect of the present invention, the lipid chamber of the multi-chamber container according to the invention comprises a structured lipid containing one or two butyric acid equivalents, such as, for example, dipalmitoyl 3-butyryl glycerol (DPBG), in a concentration of from 1 mmol to 300 mmol per liter of reconstituted multi-chamber container, wherein the total concentration of equivalent butyric acid does not exceed 301 mmol per liter of reconstituted multi-chamber container. Other examples for structured lipids which can be used according to the invention include, but are not limited to, 1-palmitoyl-2-oleoyl-3-butyryl glycerol and 1-oleoyl-2-palmitoyl-3-butyryl glycerol. In other words, the multi-chamber container according to the invention comprises arginine butyrate in the amino acid or the carbohydrate formulation (or in both), and the lipid formulation comprises a structured lipid containing one or two butyric acid equivalents, such as, for example, dipalmitoyl 3-butyryl glycerol, 1-palmitoyl-2-oleoyl-3-butyryl glycerol and/or 1-oleoyl-2-palmitoyl-3-butyryl glycerol. The final concentration of equivalent butyric acid in the reconstituted multi-chamber container should, however, again not exceed the said 301 mmol/L.

According to a further aspect of the invention, the lipid chamber of the multi-chamber container according to the invention comprises dipalmitoyl 3-butyryl glycerol (DPBG) and tributyrin, wherein the total concentration of equivalent butyric acid does not exceed 301 mmol per liter of reconstituted multi-chamber container. In other words, the multi-chamber container according to the invention comprises arginine butyrate in the amino acid or the carbohydrate formulation (or in both), and the lipid formulation comprises dipalmitoyl 3-butyryl glycerol. The final concentration of equivalent butyric acid should, however, not exceed the 301 mmol/L of reconstituted multi-chamber container.

In yet another aspect of the invention, dipalmitoyl 3-butyryl glycerol can be present in the lipid chamber as the only butyric acid derivate present in the multi-chamber container. Accordingly, the present invention also provides a multi-chamber container which comprises at least three chambers containing a carbohydrate formulation, an amino acid formulation and a lipid formulation, respectively, wherein the lipid formulation comprises DPBG in a concentration of from 1 mmol to 300 mmol per liter of reconstituted multi-chamber container. The container as well as the amino acid formulation, carbohydrate formulation and lipid formulation are otherwise as described herein. Such multi-chamber container may also comprise additional chambers, e.g. a fourth or fifth chamber with vitamins and/or trace elements.

The pH of the multi-chamber container formulations is preferably adjusted to arrive at a value of 4.5 to 8.0 in the reconstituted multi-chamber container solution, for example to a pH of 5.0, of 5.5, of 6.0, of 6.5, of 7.0, or of 7.5.

The disclosure also provides methods of treating patients who require parenteral nutrition when oral and enteral nutrition is not possible, insufficient or contraindicated. The methods involve using the multi-chamber containers and amino acid formulations disclosed herein. In particular, the methods involve parenterally administering the contents of a multi-chamber container and/or amino acid formulations as disclosed herein to a patient.

In pediatric patients, the formulations according to the present invention are administered in a way to arrive at an arginine butyrate dose of from 5 mg/kg/day to 5 g/kg/day, preferably from 5 mg/kg/day to 4 g/kg/day, or from 5 mg/kg/day to 2 g/kg/day. The dose may have to be adapted depending on the age of the pediatric patient and/or on nutrient uptake via other than the parenteral route. For example, the dose may have to be adapted or reduced if the pediatric patient additionally receives enteral nutrition.

It is to be understood that the initial doses may be low (e.g. 5 mg/kg/day) and may gradually be increased (to e.g. 100 mg/kg/day, 1 g/kg/day, 2 g/kg/day, 3 g/kg/day, 4 g/kg/day, or 5 g/kg/day) and that the doses may have to be adapted depending on nutrient uptake via other than the parenteral route, e.g. where an infant is additionally fed an infant formula and/or breastfed. Required doses can be administered, for example, by adjusting the flow rate with which TPN is administered. For example, a PN product such as NUMETA G13E can be administered with flow rates as high as 127.9 ml/kg/day. It is known that arginine butyrate, as an aqueous solution, pH 7.7, was tolerated in a dose of 3 g/kg/day during a phase I clinical trial addressing metastatic colorectal cancer patients (Douillard et al., Phase I trial of interleukin-2 and high-dose arginine butyrate in metastatic colorectal cancer. Cancer Immunology Immunotherapy 2000; 49:56-61).

In adult patients, the formulations according to the present invention are administered in a way to arrive at an arginine butyrate dose of from 5 mg/kg/day to 10 g/kg/day, preferably from 5 mg/kg/day to 5 g/kg/day, or from 500 mg/kg/day to 4 g/kg/day, or from 1 g/kg/day to 4 g/kg/day. The dose may have to be adapted depending on nutrient uptake via other than the parenteral route, e.g. if the patient additionally receives enteral nutrition. Required doses can be administered, for example, by adjusting the flow rate with which TPN is administered. For example, a PN product such as Olimel N9E (see also Examples) can be administered with a flow rate of as low as 20 ml/kg/d; for Peds, Numeta G13 with a max flow rate of 127.9 ml/kg/d.

Preferably, the maximum dose of arginine butyrate is 4 g/kg/d, and especially preferably 3 g/kg/d.

The small intestine has three different regions: the duodenum, jejunum, and ileum. The duodenum, the shortest, is where the absorption of compounds through small finger-like protrusions called villi is prepared and where it starts. The jejunum is specialized on absorption through its lining by enterocytes: small nutrient particles which have been previously digested by enzymes in the duodenum are taken up. The main function of the ileum is to absorb compounds such as vitamin B12, bile salts, and other products of digestion which were not absorbed by the jejunum. Villi are projections into the lumen covered predominantly with the above mentioned mature, absorptive enterocytes, along with occasional mucus-secreting goblet cells. Each villus is approximately 0.5-1.6 mm in length (in humans) and has many microvilli projecting from the enterocytes of its epithelium which collectively form the striated or brush border. Each of these microvilli are much smaller than a single villus. The intestinal villi are again much smaller than any of the circular folds in the intestine. Crypts are moat-like invaginations of the epithelium around the villi and are lined largely with younger epithelial cells which are involved primarily in secretion. Importantly, toward the base of the crypts are stem cells, which continually divide and provide the source of all the epithelial cells in the crypts and on the villi.

Figure 19:
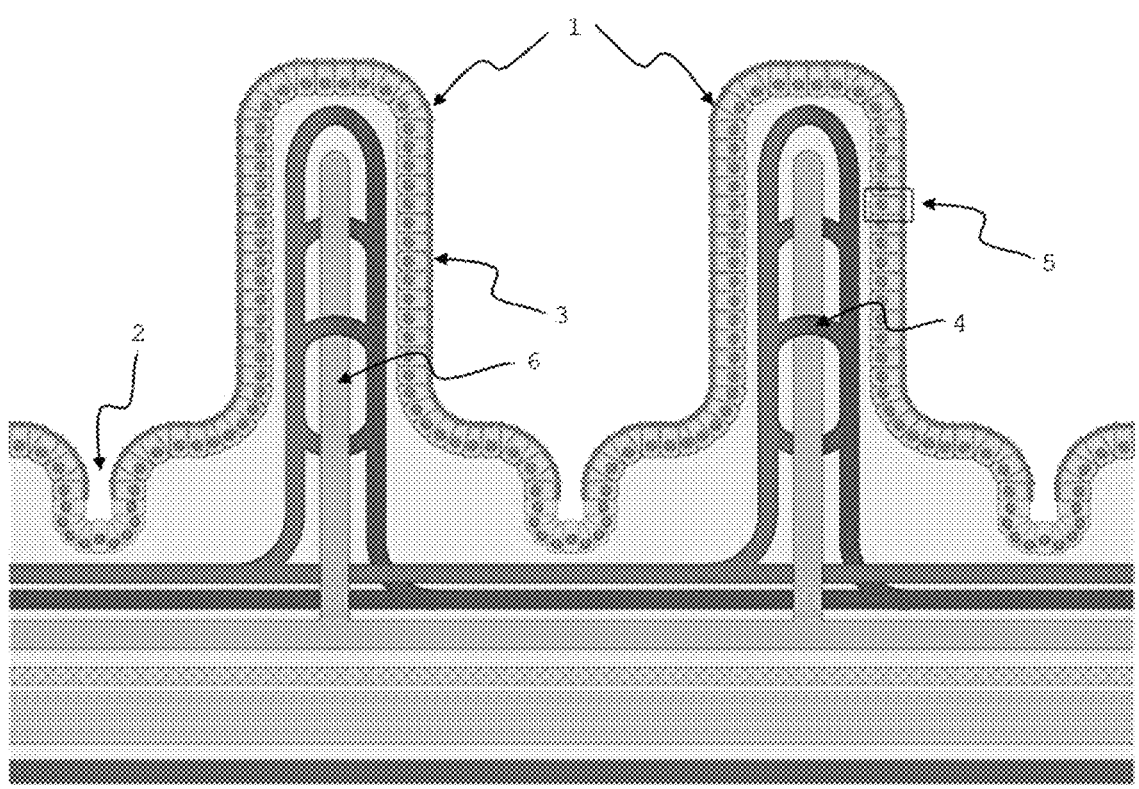
FIG. 19 is a schematic depiction of some features of the small intestine wall, some of which have been investigated also in the context of the present invention. The single-layer epithelium (3), comprising cells (5) which carry microvilli on the lumen side, forms the outer layer of the lumen side of the intestine. The intestine is characterized by protruding villi (1) and by crypts (2). The villi are interlaced with blood vessels (4), which allow for a rapid transport of absorbed products. The lacteals (6) absorb lipids from the intestine to the lymphatic system.

Healthy villi and crypts, together with their cell lining (FIG. 19), are an important marker for a functional small intestine. Villi increase the internal surface area of the intestinal walls for efficient absorption. An increased absorptive area is useful because digested nutrients (including, for example, amino acids) pass into the semipermeable villi through diffusion, which is effective only at short distances. In other words, increased surface area (in contact with the fluid in the lumen) decreases the average distance travelled by nutrient molecules and in turn increases the effectiveness of diffusion and nutrient uptake. The villi are connected to blood vessels, whereby nutrients can be transported away. Atrophied villi tend to be shorter and crypts tend to be less pronounced, with a lower depth. Accordingly, assessing the length of villi and the depth of crypts in the various sections of the small intestine, i.e. the duodenum, jejunum and the ileum, provide for a relevant information on the health of the small intestine (Burrin et al., Translational Advances in Pediatric Nutrition and Gastroenterology: New Insights from Pig Models. *Annu Rev Anim Biosci* 2020; 8:321-354). Total PN is connected to shorter villi and crypts, more goblet cells, increased inflammation and immune cells, increased intercellular permeability and reduced blood flow.

As further described in Example 3.2, Villus height, mid-villus width, and crypt depth were accordingly measured so as to understand the influence of various short-chain fatty acids on the integrity and functionality of the intestine.

It is known also that there is a relationship between intestinal epithelial integrity and intestinal health (Thomson et al., The Ussing chamber system for measuring intestinal permeability in health and disease, *BMC Gastroenterology* 2019; 19:98). Impairment of barrier function has been linked to intestinal diseases such as, for example, ulcerative colitis and Crohn's disease. The so-called Ussing system offers an ex vivo measurement of the permeability or duodenal mucosal resistance. The system allows to measure said duodenal mucosal (transepithelial) resistance (TER), which can be determined to give an overall measurement of gut integrity. A low TER value is indicative of increased permeability. Prior studies have shown that decreased TER under inflammatory conditions was associated with down regulation of "sealing" tight junctional proteins. Accordingly, determining epithelial integrity by means of the Ussing chamber constituted one option to assess the influence of various nutritional options (e.g. EN vs PN) and various PN compositions (see Example 3.5) on gut health and specifically on local inflammatory incidents.

Data in the context of the present invention have been obtained from a study with pigs. Pigs have become increasingly important animals for modeling human pediatric nutrition and gastroenterology and complementing mechanistic studies in rodents. The comparative advantages in size and physiology of the neonatal pig have led to new translational and clinically relevant models of important diseases of the gastrointestinal tract and liver in premature infants (Burrin et al, *Annu Rev Anim Biosci* 2020; 8:321-354). Therefore, comparative data to assess efficacy of different SCFA in PN as well as of SCFA-PN against standard PN and normal uptake of nutrition on gut barrier property, local and systemic inflammation and immunity as well as gut cellular architecture have been obtained based on a pig model (non-resected model, neonate pigs). Experiments were performed as described further in Example 1.

In said study for evaluating arginine butyrate in comparison to standard parenteral nutrition and other butyric acid derivatives, specifically tributyrin and dipalmitoyl 3-butyryl glycerol, the effects on gut barrier functionality and related local and systemic effects on inflammation and immunity were determined (see Examples). Table 2 summarizes the high-level results of the Study, which show that all Intervention Groups (Groups which received PN with butyric acid derivative supplemented formulations) showed better results in terms of gut architecture, systemic and local inflammation and systemic and local immunity than the Group which obtained standard PN. Some of these effects have been described before in similar studies which mostly focused on the effect of butyrate provided as sodium butyrate or tributyrin. Surprisingly, a significant difference was found for formulations comprising arginine butyrate, a butyric acid derivative which so far has not been used in parenteral nutrition compositions. Arginine butyrate proved to be especially beneficial regarding gut architecture, as evidenced by villus height, crypt depth and tight junctions (duodena mucosal resistance) analysis; local and systemic inflammation as shown by determination of pro-inflammatory and anti-inflammatory cytokines, and an improved local immunity as evidenced by sIgA. No difference for cognitive effects or brain development could be found for the respective intervention Groups.

TABLE 2

Summary of effects found in the Intervention Groups receiving PN with different butyric acid derivatives.

| | Group A (Tributyrin 10 mmol/L) | Group B (Tributyrin 30 mmol/L) | Group C (Arginine Butyrate 10 mmol/L) | Group D (Dipalmitoyl butyryl glycerol 10 mmol/L |
|---|---|---|---|---|
| Tight junctions | − | − | ++ | − |
| Villus (total) | − | − | ++ | + |
| Crypt (total) | − | ++ | + | + |
| Pro-inflammatory cytokines | − | + | ++ | + |
| Anti-inflammatory cytokines | − | + | ++ | − |
| IgA | ++ | ++ | ++ | ++ |
| Cognitive | − | − | − | − |
| Brain | − | − | − | − |

+ denotes a positive effect (compared to standard PN),
++ a very positive effect.
− denotes no difference.
Results are indiated vor villus height and crypt depth as "total", which covers results for all sections reviewed (duodenum, jejunum, ileum, colon).

An immediate high-level comparison of the results in Intervention Group C, that received arginine butyrate, and the results intervention groups A and B, that received tributyrin which is known as potentially having positive effects on gut health, versus standard PN and enteral feeding (EN) supports the finding that arginine butyrate containing formulations have an unexpected superior effect on the tested markers for gut barrier functionality, local inflammation, local immunity, gut architecture and systemic inflammation (Table 3). Tendencies shown in Table 3 for systemic inflammation will be further investigated.

TABLE 3

High-level comparison between the effects of arginine butyrates and tributyrin on selected markers for gut barrier functionality, local inflammation, local immunity, gut architecture and systemic inflammation.

| Relevance | Marker/Test | Arginine Butyrate[1] (10 mmol/L) | Tributyrin[1] 10 mmol/L | Tributyrin[1] 30 mmol/L |
|---|---|---|---|---|
| Gut barrier functionality | Duodenal Mucosal Resistance (Ussing chamber) | ++[2] | = | = |
| Local inflammation | Jejunal Cytokine Concentration (less pro-inflammatory cytokines Il-1β, Il-6, TNF-α | +++ | +++ | +++ |
| | Jejunal Cytokine Concentration (more anti-inflammatory cytokines Il-8, Il-10) | ++ | = | + |
| | Ileal Cytokine Concentration (less pro-inflammatory cytokines Il-1β, Il-6, TNF-α | +++ | ++ | ++ |
| | Ileal Cytokine Concentration (more anti-inflammatory cytokines Il-8, Il-10) | +[4] | + | = |
| Local immunity | Jejunal sIgA Concentration | +++[3] | ++[5] | ++[5] |
| Gut architecture | Total villus height | + | + | + |
| | Total crypt depth | + | + | + |
| Systemic inflammation | | tbd[6] | tbd[6] | tbd[6] |

+++ indicate P < 0.01;
++ indicates P < 0.05;
+ indicates positive trends;
= denotes no significant P value;
− denotes negative trends.
[1] compared to standard PN (s-PN).
[2] as good as enteral feeding;
[3] better than enteral;
[4] less pro-inflammatory cytokines, downregulation of anti-inflammatory secretion;
[5] close to enteral;
[6] same trends as for local inflammation, to be further confirmed.

Accordingly, in pediatric patients, particularly in full-term neonates and pre-term infants, the formulations according to the present disclosure can be used to support the development of a healthy intestinal morphology and/or growth and/or body composition. Furthermore, they can support immune response and gut flora. They are also useful for the resolution of inflammation and they improve nutrient utilization. They may also be used in the prevention or treatment of sepsis, chronic lung disease, cachexia, inflammatory diseases and/or necrotizing enterocolitis.

While the formulations according to the present disclosure are particularly useful in providing parenteral nutrition to infants, specifically pre-term neonates, they may also be used to provide total or partial parenteral nutrition to adults.

The formulations according to the invention specifically support adult patients' local and systemic immune response, gut flora, and reduce local inflammation. Accordingly, they can be used for the resolution of inflammation and to improve nutrient utilization in patients being at risk of or who have already developed inflammation. Further, they may be used in the prevention or treatment of sepsis, chronic lung disease, cachexia, or inflammatory diseases. For example, the formulations according to the invention may be used in the treatment or prevention of cachexia and/or reduced immune response in cancer patients, of sepsis in critically ill patients (e.g., on short-term parenteral nutrition who is covering 95-100% of the energy needs from parenteral nutrition, a patient suffering from sepsis or septic shock), of metabolically stressed patients, or of parenteral nutrition associated issues in patients with short bowel syndrome or intestinal failure. They may also be used to support immune response in critically ill patients (e.g., on short-term parenteral nutrition who is covering 95-100% of the energy needs from parenteral nutrition, a patient suffering from sepsis or septic shock), to support immune response in cancer patients, to support immune response in immunodeficient patients, to support gut flora in metabolically stressed patients and to improve nutrient utilization in malnourished patients.

It is known (WO 2019/0232054 A1, WO2019/232044 A1) that lipid emulsion comprising choline derivatives have the potential to avoid and/or treat hepatic steatosis which may lead to liver metabolic dysfunction, inflammation, and advanced forms of nonalcoholic fatty liver disease (NAFLD) and which is an issue specifically in parenteral nutrition, especially in the treatment of pediatric patients but also in adult patients. NAFLD includes a spectrum of disease from simple steatosis to nonalcoholic steatohepatitis (NASH), which can progress to cirrhosis and hepatocellular carcinoma. Accordingly, the multi-chamber containers according to the invention which comprise a lipid emulsion in a third chamber and which additionally contain choline derivatives, preferably choline chloride or GPC, can address two major issues arising in the total parenteral nutrition of patients, specifically of pediatric patients. Therefore, the present disclosure is also providing methods for treating hepatic steatosis, liver metabolic dysfunction, inflammation, and advanced forms of nonalcoholic fatty liver disease (NAFLD) in pediatric and/or adult patients. Specifically, the multi-chamber containers and the formulations comprised therein can be used to treat long-term TPN patients who have developed or are at risk of developing both hepatic steatosis, liver metabolic dysfunction, inflammation, and advanced forms of nonalcoholic fatty liver disease (NAFLD) and a reduced gut barrier, degradation of the gut architecture, are suffering from incidents of chronic or acute inflammation (local and systemic) and have developed or at risk of developing a reduced local and systemic immunity.

The formulations according to the invention can be administered according to methods known in the art, for example, through central or peripheral catheters, or can be administered subcutaneously.

EXAMPLES

Example 1: Materials and Methods

A pig model was chosen to assess the effects of enteral, standard parenteral, and parenteral nutrition wherein the standard PN formulation was supplemented with various butyrate derivatives (see Table 4). It is currently estimated that pre-term pigs born at 90% gestation are comparable to human pre-term infants at 75% gestation (30-32 weeks) (Burrin et al., Translational Advances in Pediatric Nutrition and Gastroenterology: New Insights from Pig Models. Annu Rev Anim Biosci 2020; 8:321-354).
1.1 Study Design Neonatal Yorkshire/Landrace cross bred piglets (n=72; six at a time from the same litter, repeating 12 times) were obtained from Oak Hill Genetics (Ewing, Ill.) after 48-hour sow reared for colostrum consumption and iron supplementation. Piglets were randomized into Groups (12 piglets per group) to receive 10 days of nutrition as shown in Table 4.

TABLE 4

Nutrition provided to groups of piglets over 10 days.

| Group | Nutrition | Description |
|---|---|---|
| E | Milk replacer feeding taken ad libidum | "Normal nutrition" |
| P | Olimel N9E | "Standard PN" |
| A | Olimel N9E + Tributyrin 10 mmol/L TPN | Tributyrin provided in lipid chamber; "TB-PN" |
| B | Olimel N9E + Tributyrin 30 mmol/L TPN | Tributyrin provided in lipid chamber; "TB-PN" |

TABLE 4-continued

Nutrition provided to groups of piglets over 10 days.

| Group | Nutrition | Description |
|---|---|---|
| C | Olimel N9E + Arginine butyrate 10 mmol/L TPN | Arginine butyrate provided in amino acid chamber "AB-PN" |
| D | Olimel N9E + 1,2-Dipalmitoyl 3-butyryl glycerol 10 mmol/L TPN | 1,2-Dipalmitoyl 3-butyryl glycerol provided in lipid chamber (DPBG-PN) |

The formulations used were all based on Olimel N9E (see Table 4). Supplementation with tributyrin and 1,2-dipalmitoyl 3-butyryl glycerol was provided in the lipid chambers of the 3CB product Olimel N9E, whereas arginine butyrate was added to the amino acid chamber. All concentrations given relate to the final reconstituted solution (TPN). Accordingly, the administered formulations and concentration are fully comparable, irrespective of the initial chamber to which the supplementation was added. To each bag of Olimel N9E that was administered, one bulk package Infuvite Pediatric (Baxter Healthcare Corp.) comprising vitamins for intravenous infusion after dilution was added. Also added to each bag of Olimel N9E was one vial MICRO +6 Pediatric Injection (Baxter Healtchare Corp.) comprising trace elements.

TABLE 5

Compositions used in the study.

| Composition | Formulation Group A | Formulation Group B | Formulation Group C | Formulation Group D |
|---|---|---|---|---|
| Butyrate Derivative | Tributyrin (10 mmol/L TPN) (5 g/L LE) | Tributyrin (30 mmol/L TPN) (15 g/L LE) | Arginine butyrate (10 mmol/L TPN) (6.6 g/L amino acids) | 1,2-Dipalmitoyl 3-butyryl glycerol (10 mmol/L TPN) (32 g/L LE) |
| Amino Acid Chamber concentration | 14.2% | 14.2% | 14.5% | 14.2% |
| Carbohydrate Chamber concentration | 27.5% | 27.5% | 27.5% | 27.5% |
| Lipid Chamber concentration | 20.5% | 21.5% | 20.0% | 23.2% |
| Total Kcal per L TPN | 1037 kCal/L | 1055 kCal/L | 1031 Kcal/L | 1085 Kcal/L |

LE means Lipid Emulsion.
Underlined values indicate which component of Olimel N9E was changed due to the addition of the supplement.
Olimel N9E alone: Amino Acid Chamber: 14.2%; Carbohydrate Chamber 27.5%; Lipid Emulsion Chamber 20.0%

Butyrate concentrations were chosen in a range which was known to be tolerated well in a similarly structured study (Bartholome et al, J Parent Nutr 2014; 28(4):210-223). Formulations were provided to achieve a daily amino acid content of 12.9 g/kg/day, with a daily infusion rate of 253 Kcal/kg/day. Only on day 1, immediately following surgery in order to minimize risk of malnutrition, the infusion rate was 307 Kcal/kg/day. A study period of 10 days was chosen due to the typical intestinal epithelial cell turnover time of 5-7 days in order to capture a complete cell turnover cycle.
1.2 Surgical Procedure Upon arrival (Day 1), piglets underwent central line placement. A 3 cm incision was made in the right clavicular region to isolate the external jugular for catheter insertion (3.5 French polyvinyl chloride catheter). After blunt dissection, the jugular vein was ligated with two 3-0 silk sutures placed cranial (anatomically closer to head) and cardial (anatomically closer to heart) to the central line insertion site. Once the cranial ligature had been tied, a small incision was made in the jugular vein to insert a pre-measured central line (3.5 French PVC catheter) and was inserted 6 cm (premeasured and marked at 6 cm) through the external jugular in the super vena cava for PN infusion. Following central line placement, cardial suture was tied in order to immobilize the line, and the terminal end was tunneled subcutaneously to exit between the scapulae. Once placed, the central line was flushed with heparinized saline until attached to the PN pump. The incision site was closed in a single-layer closure using vicryl in a running subcuticular suture pattern. Suture sites were monitored and covered with petroleum jelly overlayed with sterile gauze anchored with Transpore tape.

1.3 Animal Care and Housing

Animals were allowed to recover under constant supervision and monitored for respiration rate, heart rate, signs of pain, and ensure regaining of consciousness. Following recovery, piglets will be fitted with jackets with the swivel tether (Lomir Biomedical Inc., Quebec, Canada) attached to protect the catheter and infusion lines to allow for free mobility. No presurgical jacket acclamation was done due to the young age and need to minimize time without nutrition and hydration. PN was be administered to provide 307 Kcal/kg/day immediately following surgery in order to minimize risk of malnutrition. The dosage of PN was 120% (20% higher) than the nutrition requirements for piglets of this age and size (200 Kcal/kg/day) to compensate for surgical stress. Each day, the animals underwent clinical assessment for both research and animal health purposes. A full clinical assessment was be performed every morning: weight (grams), girth (cm), body temperature, respiration rate, heart rate, activity level, healing of catheter insertion site and animal behavior and pain scores. A partial clinical assessment (minus weight and girth measurements) was performed each evening to reevaluate the wellness of the piglets.

1.4 Nutrient Interventions

Milk replacer (OptiLac Baby Pig Milk Replacer; Hubbard Feeds, Mankato, Minn., U.S.A.) were prepared fresh daily per manufacturer recommendation. Volume of milk replacer was calculated based on daily morning weight to provide 253 kcal/kg. The prepared volume of milk replacer was provided to Group E to be taken ad libidum.

Figure 2:
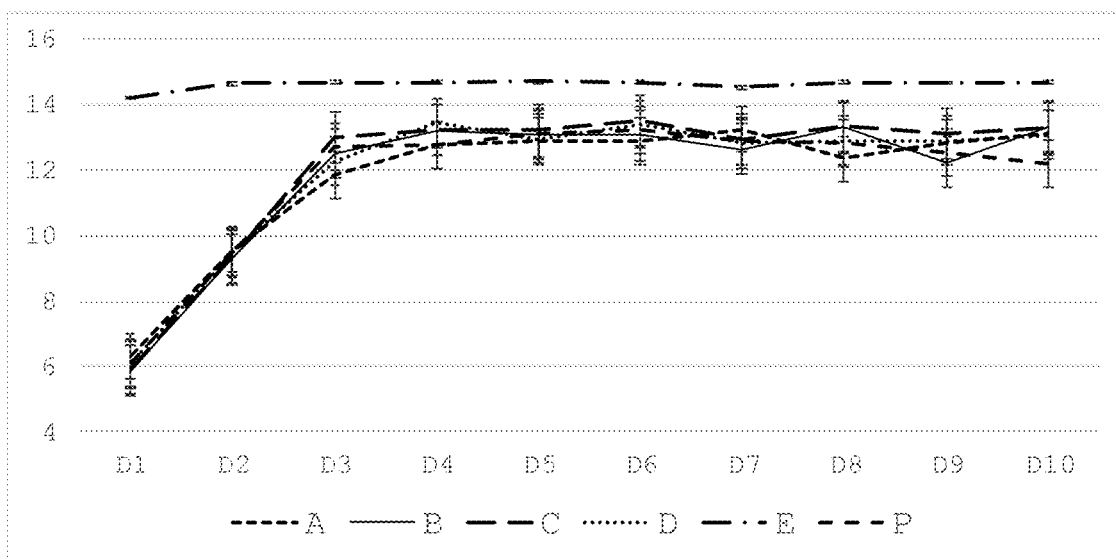
FIG. 2 shows the average protein delivered to piglets in Groups A, B, C, D, E or P (see Table 4) in g protein/kg body weight/day over 10 days (D1 through D10). Group E refers to the piglets which were fed with milk replacer ad libitum. Group P refers to the group on standard parenteral nutrition (S-PN), whereas Groups A, B, C and D received SCFA-PN, i.e. parenteral nutrition wherein the composition administered was supplemented with tributyrin at 10 mmol/L (Group A) or 30 mmol/L (Group B), arginine butyrate at 10 mmol/L (Group C) and 1,2 dipalmitoyl 3-butyryl glycerol at 10 mmol/L (Group D). The amount of protein delivered was comparable for all piglets on S-PN or SCFA-PN.

All PN solutions were compounded by the manufacturer (Baxter Healthcare Corp.) as a 3-in-1 solution (bag volume: 1000 mL) and delivered at the start of each experiment cycle and kept at 40° C. during administration. Each PN solution contained dextrose, amino acids, and a lipid emulsion in separate compartments until use. PN solutions also contained vitamins, minerals, and experimental amounts of butyric acid derivatives as assigned (Table 4 and 5). All PN solutions were infused continuously using AVA 6000CMS MultiTherapy infusion pumps (AVA Biomedical, Wilmette, Ill.) to provide 253 kcal/kg/day and 12.8 grams amino acids/kg/day. All milk replacer feedings and PN infusions were provided to ensure isocaloric provision for all piglets. Average energy delivery (FIG. 1) and average protein delivery (FIG. 2) were documented. The Figures demonstrate that the Study Groups were investigated under the same conditions.

1.5 Cognitive Assessment

Figure 14:
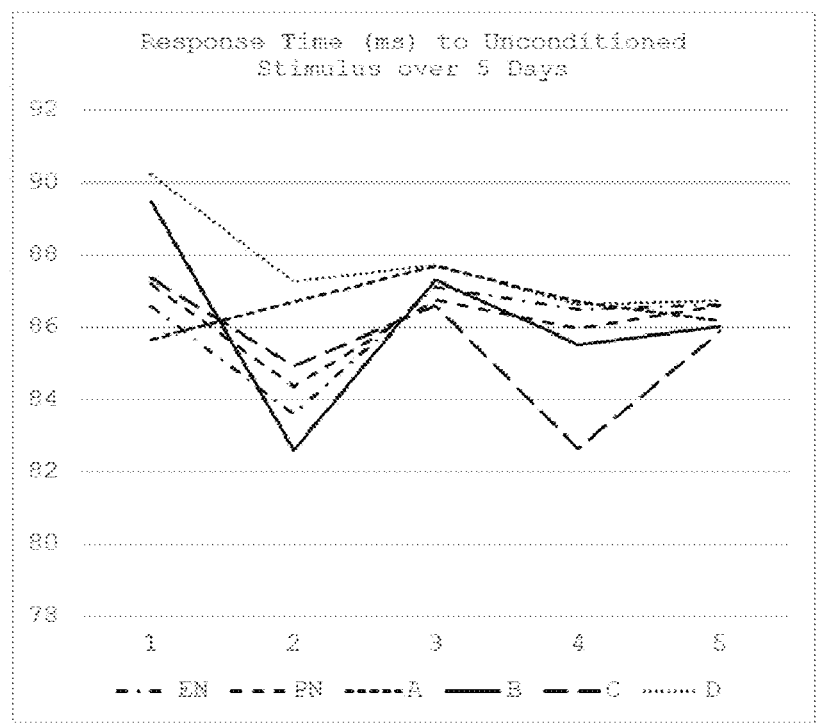
FIG. 14 provides for CS response times of the piglets from the respective groups, which is used for the assessment of cognitive function.
Figure 14:
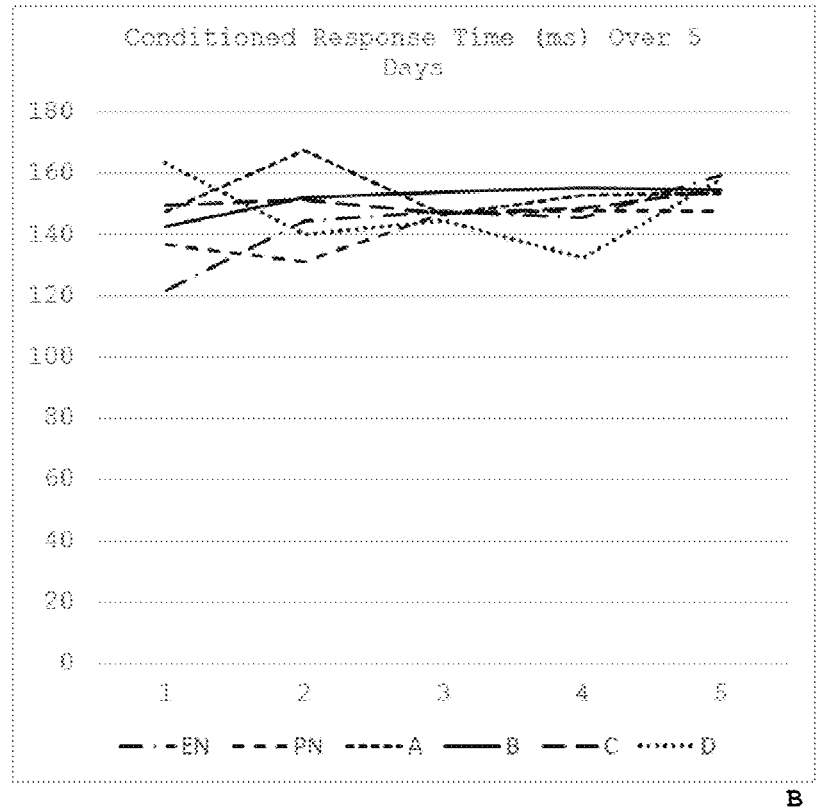

Eyeblink conditioning is an established Pavlovian method to assess the cerebellum and associated brainstem circuitry with hippocampus involvement that are essential for learning and memory. The eyeblink conditioning procedure took place in a sound-attenuating chamber. A fan was inside the chamber and ran throughout the experiment for ambient noise (70 dB). A speaker mounted to the wall of the chamber delivered the tone conditioned stimulus (CS). A small plastic air puff delivery nozzle (San Diego Instruments, San Diego, Calif.) was secured at approximately 2 cm from the piglet's left eye to deliver the unconditioned stimulus (US). After adaptation to the conditioning apparatus on study day 3, a total of five CS-US conditioning sessions occurred on study days 4-8 following. Each conditioning session consisted of 90 CS-US paired trials and 10 CS alone trials for a total of 100 trials/session. Every tenth trial was a CS alone trial. The CS-US paired trials included: a 500 ms auditory CS (1 kHz, 85 dB tone), a 400 ms interstimulus interval (ISI), followed by a 100 ms corneal airpuff US (10 psi). Both the CS and US were co-terminated at the exact same time. The CS alone trials consisted of a 500 ms auditory CS (1 kHz, 85 dB tone) only. There were random inter-trial intervals of 20 seconds throughout each session. Each conditioning session lasted no longer than 35 minutes. The San Diego Instruments eyeblink software was used to record conditioning session moment-to-moment infrared-reflectance data. The results are shown in FIG. 14. No significant differences were detected between the Groups.

1.6 Brain Structure Development and Body Composition Assessment

Figure 3:
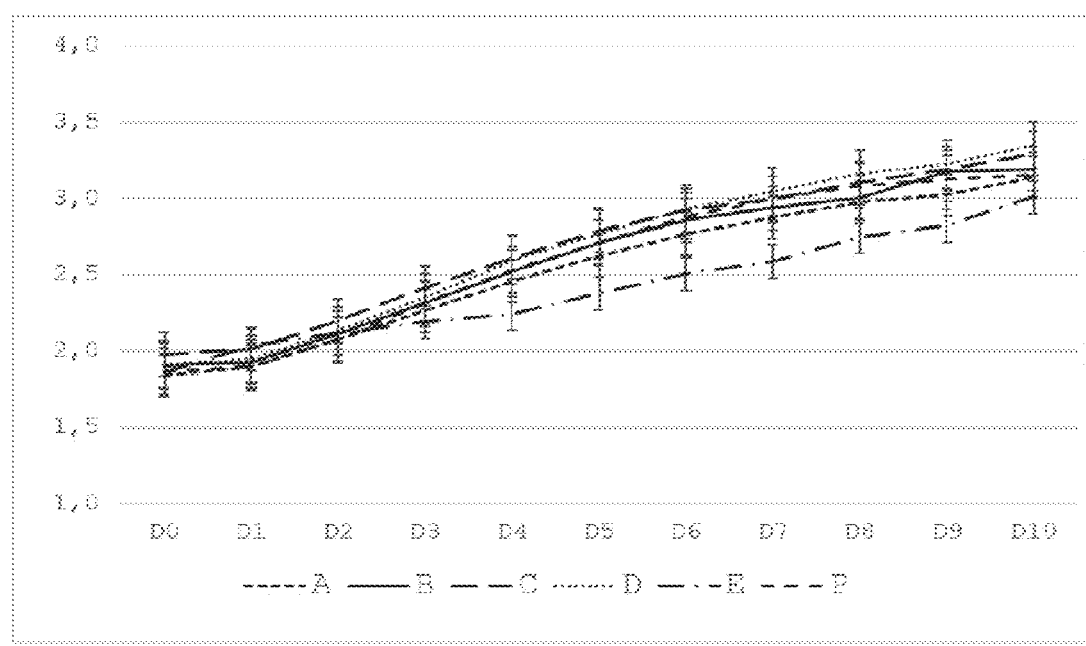
FIG. 3 shows the average development of body weight in kg over the study period (10 days, starting on D0 which is the day of central catheter placement) of piglets in Groups A, B, C, D, E or P (see Table 4). Group E refers to the piglets which were fed with milk replacer ad libitum. Group P refers to the group on standard parenteral nutrition (S-PN), whereas Groups A, B, C and D received SCFA-PN, i.e. parenteral nutrition wherein the composition administered was supplemented with tributyrin at 10 mmol/L (Group A) or 30 mmol/L (Group B), arginine butyrate at 10 mmol/L (Group C) and 1,2 dipalmitoyl 3-butyryl glycerol at 10 mmol/L (Group D). Body weight developed similarly in all groups.
Figure 4:
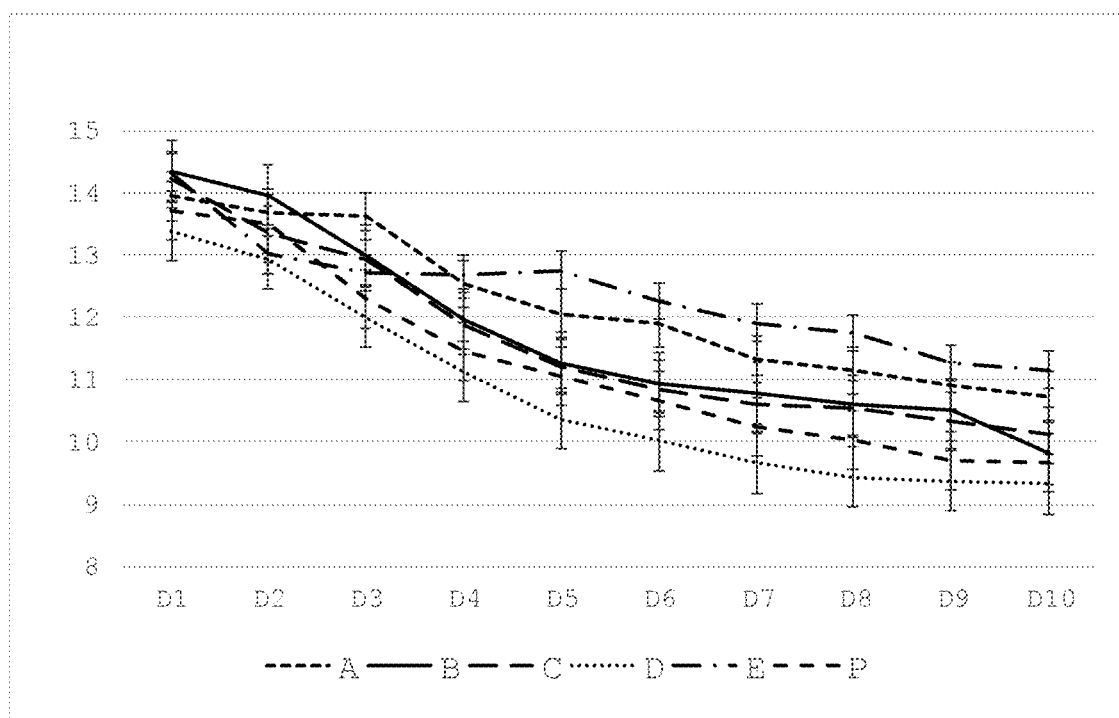
FIG. 4 shows the average development of abdominal girth in cm/kg body weight over the study period (10 days, D1 through D10) of piglets in Groups A, B, C, D, E or P (see Table 4). Group E refers to the piglets which were fed with milk replacer ad libitum. Group P refers to the group on standard parenteral nutrition (S-PN), whereas Groups A, B, C and D received SCFA-PN, i.e. parenteral nutrition wherein the composition administered was supplemented with tributyrin at 10 mmol/L (Group A) or 30 mmol/L (Group B), arginine butyrate at 10 mmol/L (Group C) and 1,2 dipalmitoyl 3-butyryl glycerol at 10 mmol/L (Group D). Abdominal girth developed similarly in all groups.

On study day 9, the piglets were submitted to Magnetic Resonance Imaging (MRI) using an Agilent 9.4 Tesla MRI system (Santa Clara, Calif.) to assess brain structural development and body composition. Heart rate and respiration were monitor during the entire MRI scan. For anatomic assessment of the brain targeting the hippocampus, images were obtained using a 3D T1-weighted magnetization prepared gradient-echo sequence: repetition time=1,900 ms; echo time=2.48 ms; inversion time=900 ms, flip angle=9°, matrix=256×256 (interpolated to 512×512), slice thickness=1.0 mm. For body composition assessment, a multi-slice, spin-echo technique was used to image the truncal area (longissimus fat/muscle): echo time=20 ms; recovery time=400 ms with four-signal averaging. Each image had a slice thickness of 4.9 mm with no gap between images. Total imaging time did not exceed one hour per piglet. Total scanning time was approximately 60 minutes to include both brain and body composition scanning. The MRI images were analyzed using OsiriX (Bernex, Switzerland). It was found that the brain structure did not show any significant differences between the Study Groups. The average body weight and abdominal girth of the piglets in the Study Groups was also monitored. FIG. 3 shows that the body weight developed similarly in all Study Groups. FIG. 4 shows that also the average abdominal girth developed similarly in the Study Groups.

1.7 Study Sample Collection

Figure 5:
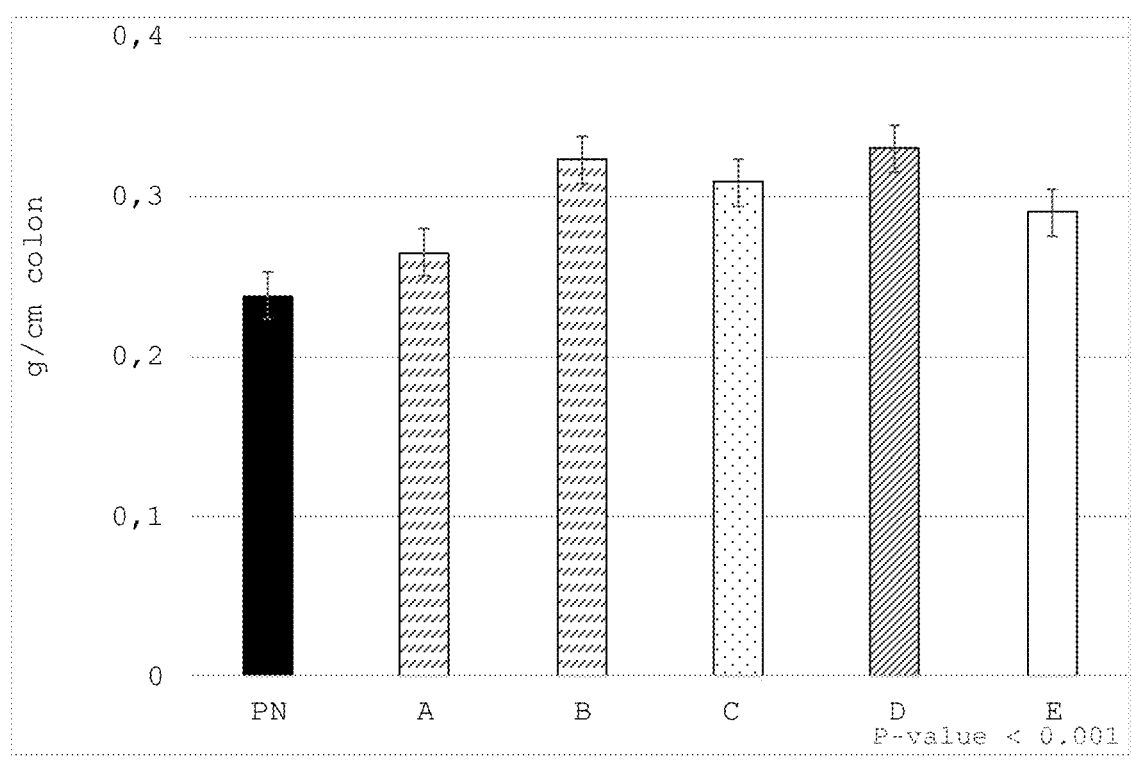
FIG. 5 shows the average colonic weight in g/cm colon over the study period (10 days, starting on D0 which is the day of central catheter placement) of piglets in Groups A, B, C, D, E or P (see Table 4). Group E refers to the piglets which were fed with milk replacer ad libitum. Group P refers to the group on standard parenteral nutrition (S-PN), whereas Groups A, B, C and D received SCFA-PN, i.e. parenteral nutrition wherein the composition administered was supplemented with tributyrin at 10 mmol/L (Group A) or 30 mmol/L (Group B), arginine butyrate at 10 mmol/L (Group C) and 1,2 dipalmitoyl 3-butyryl glycerol at 10 mmol/L (Group D). Outcome was evaluated based on grouping information using Fisher's LSD test. Groups that do not share a letter are significantly different.

Upon completion of the study period, animals were euthanized by lethal injection (1 mL/10 lb; Fatal Plus; Veterinary Laboratories, Inc, Lenexa, Kans.) delivered via the central line. Urine and blood samples were collected for chemistry, high-performance liquid chromatography (HPLC), and enzyme-linked immunosorbent assay (ELISA) measurements. The gastrointestinal tract was removed and separated into different anatomic segments for histomorphology, electrophysiology, nutrient transport, and ELISA tests. Kidneys, liver, spleen, and muscle samples were also taken from each piglet for histology and chemistry assessments. Stool samples were collected and stored for microbiota analyses. The average colonic weight of the Study Groups was determined (FIG. 5). Here, the Groups A to D which had obtained butyric acid derivative supplemented PN and the Group that had received enteral feeding were superior to Group PN that has obtained standard PN.

Example 2: PN Compositions

Compositions used are described in Table 4 and Table 5. After compounding of the respective butyrate derivatives into the respective chambers of the bags and following sterilization, free butyric acid was measured in the lipid chamber (for tributyrin and DPBG compositions) and the butyrate content in the amino acid chamber was determined.

well-oriented villi and crypts. Villus surface area (villus height×midvillus width) was also calculated. In addition, intestinal segment circumference was measured to estimate intestinal surface area. The results are provided in FIGS. 7 through 12 (see there for details). Table 6 shows the results of the histomorphological analysis of the Study Groups. The Table summarizes the average difference (in % of each Intervention Group (A, B, C, D) versus the PN Group) of the villus height and the crypt depth in the different sections of the gut, i.e. duodenum, jejunum, ileum and colon. The Intervention Groups show an improved villus height compared to the s-PN Group. In total Group C shows the most prominent improvement of the gut architecture.

TABLE 6

Histomorphological Results of the Intervention Groups, providing for the average difference (in % of each Intervention Group (A, B, C, D) versus the PN Group) of the villus height and the crypt depth in the different sections of the gut.

| % Δ from PN | Duodenum | | Jejunum | | Ileum | | Colon | Total | | |
|---|---|---|---|---|---|---|---|---|---|---|
| | C | V | C | V | C | V | C | C | V | Total |
| A | +11 | +32 | -8 | +14 | +17 | +14 | +9 | +29 | +60 | +89 |
| B | +12 | +12 | -14 | +5 | +27 | +31 | +10 | +63 | +48 | +111 |
| C | +15 | +35 | +3 | +26 | +7 | +16 | +22 | +47 | +77 | +124 |
| D | +19 | +31 | +2 | +5 | +15 | +24 | +12 | +50 | +60 | +110 |

As shown in Table 5, only very limited amounts of butyric acid were released during the sterilization of the bags. In case of the amino acid chamber, the recovery of butyrate after sterilization corresponds to what was introduced. Accordingly, no deterioration of the salt occurred during or after sterilization. In addition, the stability of the composition over time (12 months, 25° C., 40% RH) was confirmed. The free butyric acid can be quantified by GC-FID, after sample preparation by liquid-liquid extraction of the lipid emulsion or directly from amino acid solution. These methods are known in the art.

Example 3: Methods for Assessing Study Endpoints 3.1 Fisher's Least Significant Difference (LSD) Test The method of Fisher's Least Significant Difference (LSD) Test has been described, for example, by Williams and Abdi in Neil Salkind (Ed.), Encyclopedia of Research Design. Thousand Oaks, Calif.: Sage. 2010. The Fisher's LSD test is basically a set of individual tests. It is only used as a follow up to ANOVA. Following one-way (or two-way) analysis of variance (ANOVA), it is possible to compare the mean of one group with the mean of another. One way to do this is by using Fisher's Least Significant Difference (LSD) test. The test follows the principle to compute the smallest significant difference (i.e., the LSD) between two means as if these means had been the only means to be compared (i.e., with a t test) and to declare significant any difference larger than the LSD.

3.2 Histomorphology and Preparation of Ileus and Jejunum Sections

Figure 6:
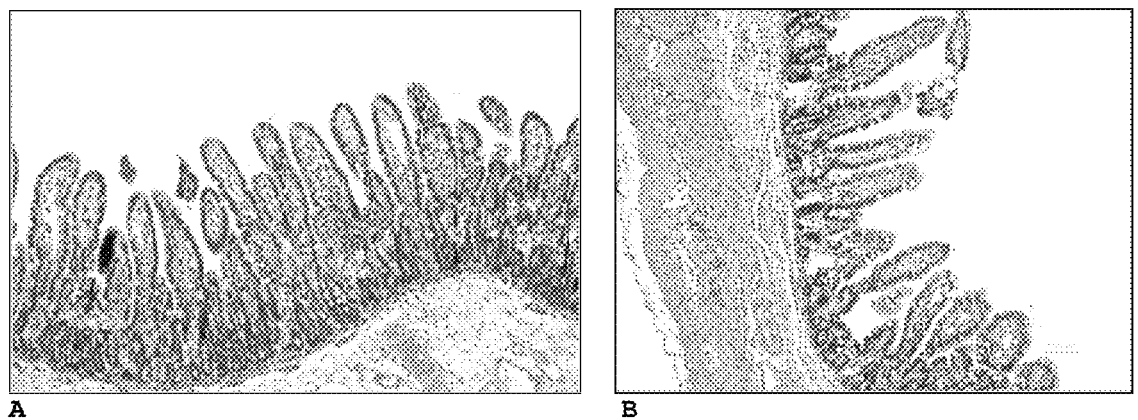
FIG. 6 shows exemplary examples of sections prepared to assess effects in the intestinal histomorphology of the jejunum (A) and the ileum (B). Sections were stained with hematoxylin and eosin. Sections were used to determine the duodenal villous length and duodenal crypt length (FIG. 7 and FIG. 8)
Figure 7:
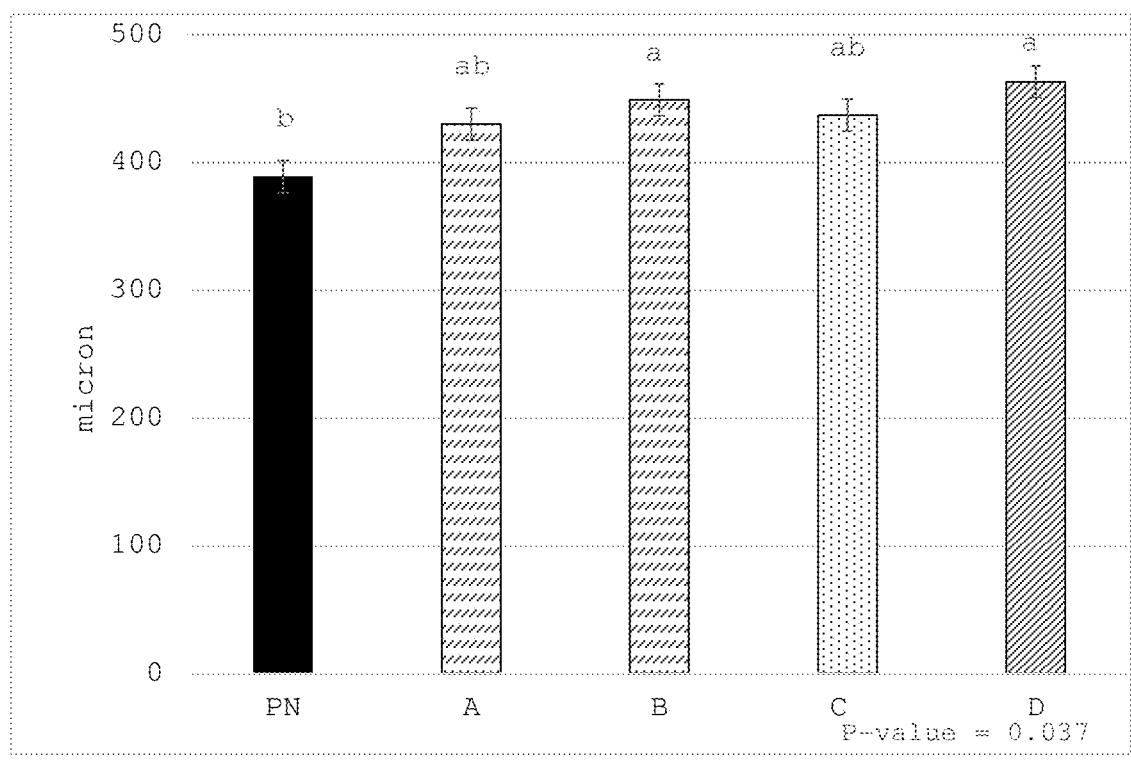
FIG. 7 shows the average duodenal villous length for the respective Study Groups A, B, C and D (see Table 4) as well as Group P which is designated "PN" in this FIG. 7. Group E is not shown. Mean duodenal villous length in Group E was 810p. Based on the analysis of data according to Fisher's LSD test, a significant difference was found for Group PN (S-PN), which results in a significantly reduced villous length, and Groups B (tributyrin supplementation, 30 mmol/L TPN, TB-PN) and Group D (1,2-Dipalmitoyl 3-butyryl glycerol supplementation, 10 mmol/L TPN, DPBG- PN), which show an increased villous length compared to the other study groups and especially compared to the PN (S-PN) group. Groups A and C showed about the same results and are only slightly below the mean values determined for Groups B and D.
Figure 8:
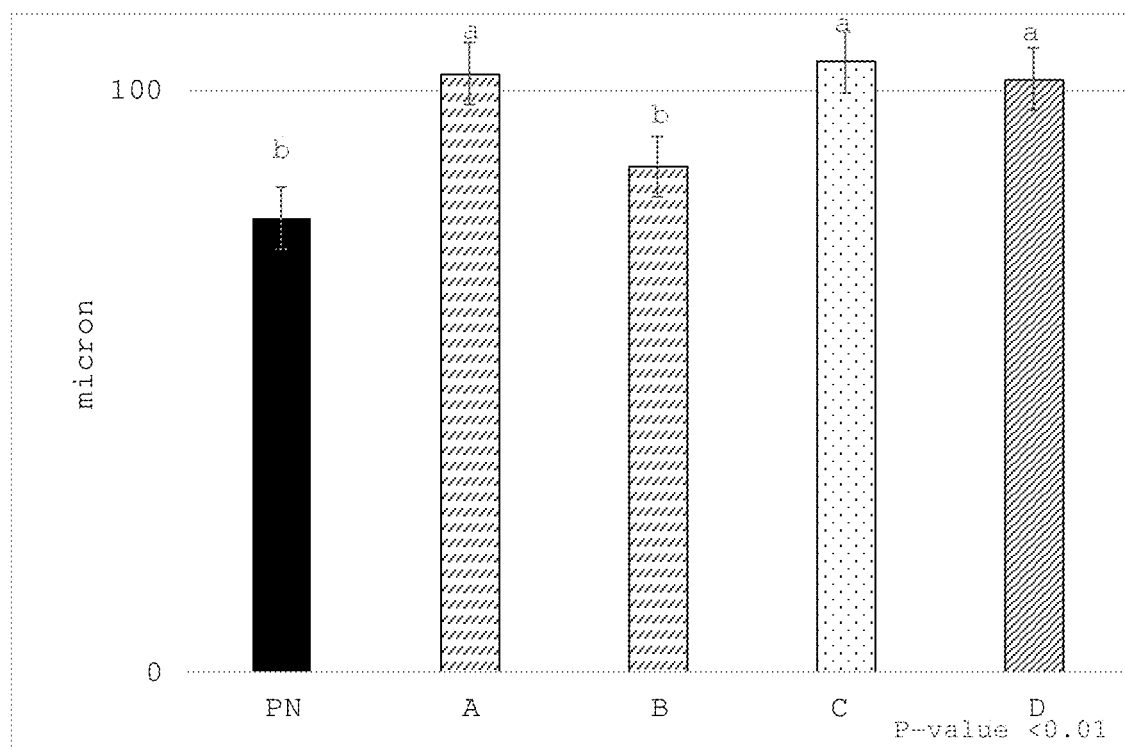
FIG. 8 shows the average duodenal crypt length for the respective Study Groups A, B, C and D (see Table 4) as well as Group P which is designated "PN" in this FIG. 8. Group E is not shown. Mean duodenal crypt depth in Group E was 152p. Based on the analysis of data according to Fisher's LSD test, a significant difference was found again for Group PN (S-PN), which shows the lowest values for crypt depth. Group A (tributyrin supplementation, 10 mmol/L TPN, TB-PN), Group C (arginine butyrate supplementation, 10 mmol/L TPN, AB-PN) and Group D (DPBG supplementation, 10 mmol/L TPN, DPBG-PN) gave the best results, with Group C being slightly better even than Groups A and D. Groups B (tributyrin supplementation, 30 mmol/L TPN, TB-PN), shows a better crypt depth than S-PN, but is not as good as Groups A, C and D.
Figure 9:
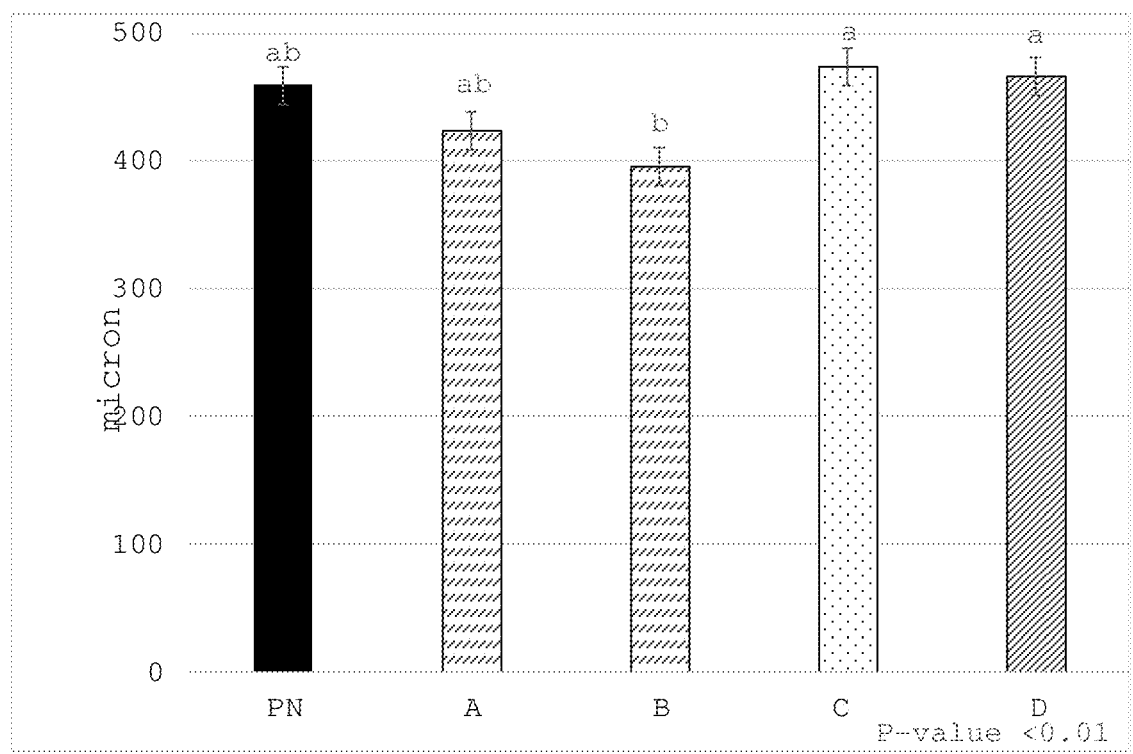
FIG. 9 shows the average jejunal villous length for the respective Study Groups A, B, C and D (see Table 4) as well as Group P which is designated "PN" in this FIG. 9. Group E is not shown. Mean jejunal villous length in Group E was 152p. Based on the analysis of data according to Fisher's LSD test, a significant difference was found especially for Group C (arginine butyrate supplementation, 10 mmol/L TPN, AB-PN), which gave the best results. Jejunal villous length was relatively low in Group B (TB-PN, 10 mmol/L TPN), whereas Group D (DPBG-PN) gave relatively good results as well.
Figure 10:
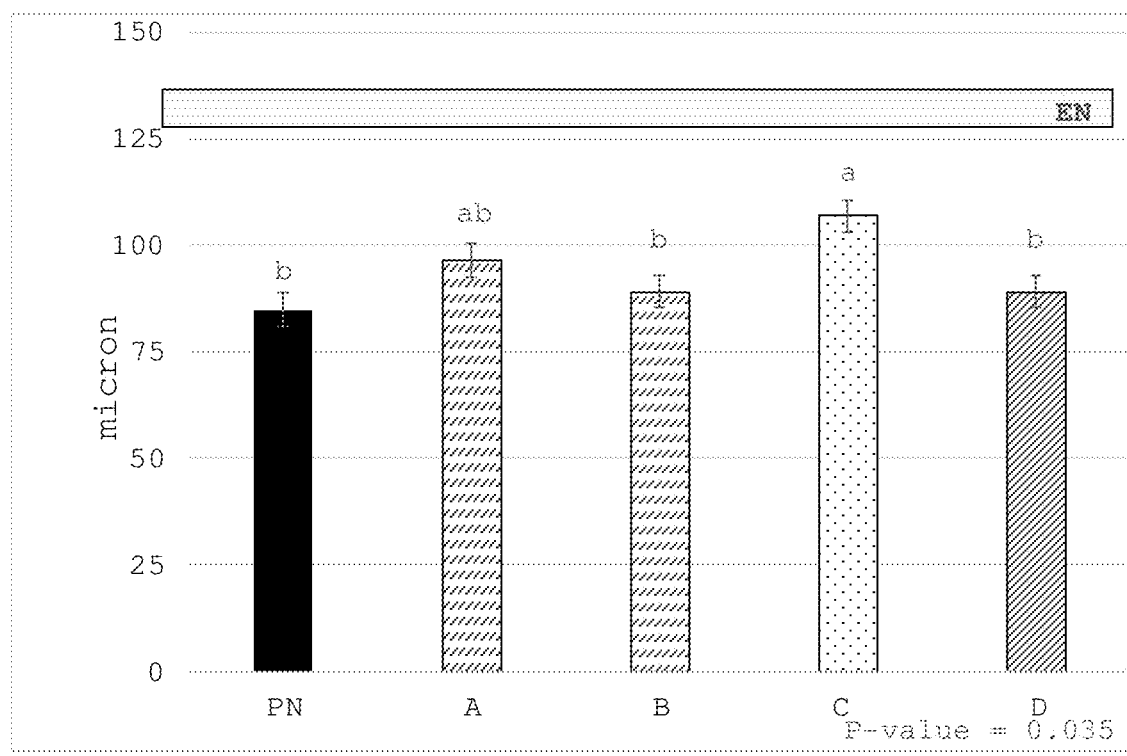
FIG. 10 shows the average jejunal crypt depth for the respective Study Groups A, B, C and D (see Table 4) as well as Group P which is designated "PN" in this FIG. 10. Mean jejunal crypt depth in case of EN is shown by a horizontal column for comparison. Based on the analysis of data according to Fisher's LSD test, a significant difference was again found especially for Group C (arginine butyrate supplementation, 10 mmol/L TPN, AB-PN), which gave the best results. Jejunal crypt depth was lower in Groups A, B, D and lowest for Group P ("PN").
Figure 11:
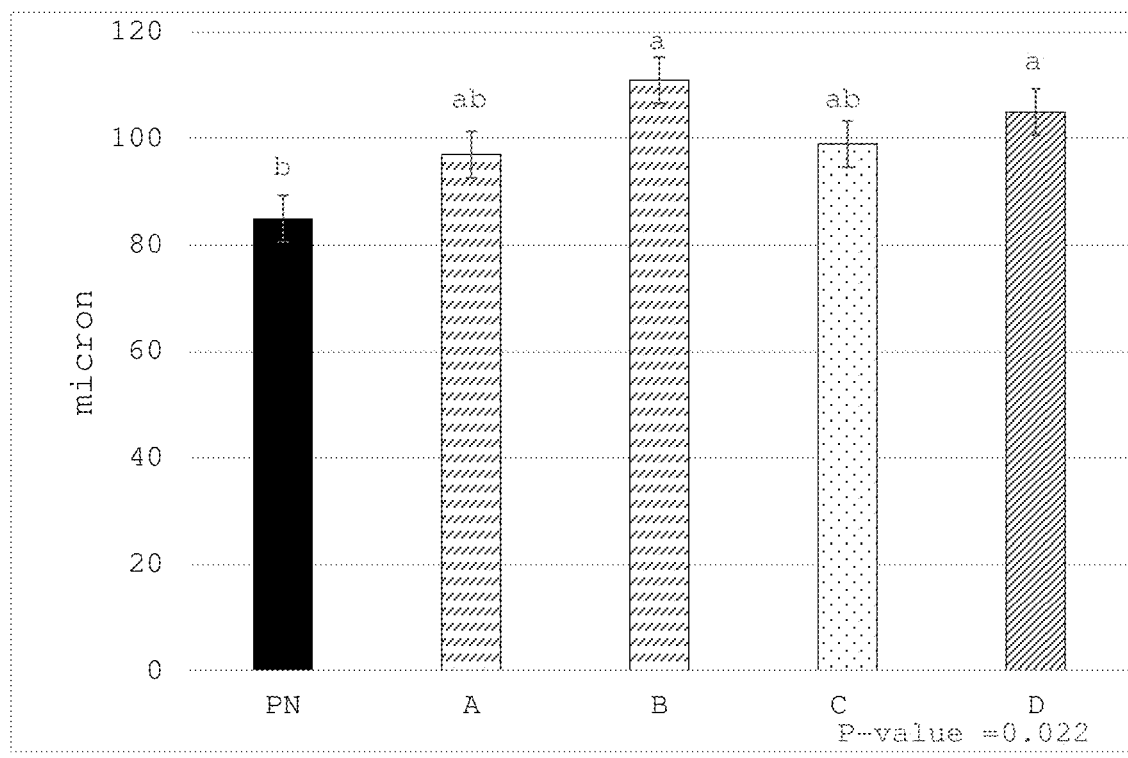
FIG. 11 shows the average ileal crypt depth for the respective Study Groups A, B, C and D (see Table 4) as well as Group P which is designated "PN" in this FIG. 11. Mean jejunal crypt depth in case of EN is 155p. Based on the analysis of data according to Fisher's LSD test, a significant difference was found for Group A (tributyrin supplementation, 10 mmol/L TPN, TB-PN) and Group D (1,2-Dipalmitoyl 3-butyryl glycerol supplementation, 10 mmol/L TPN, DPBG-PN), with Group C being close behind. Jejunal crypt depth was again lowest in Group P ("PN").
Figure 12:
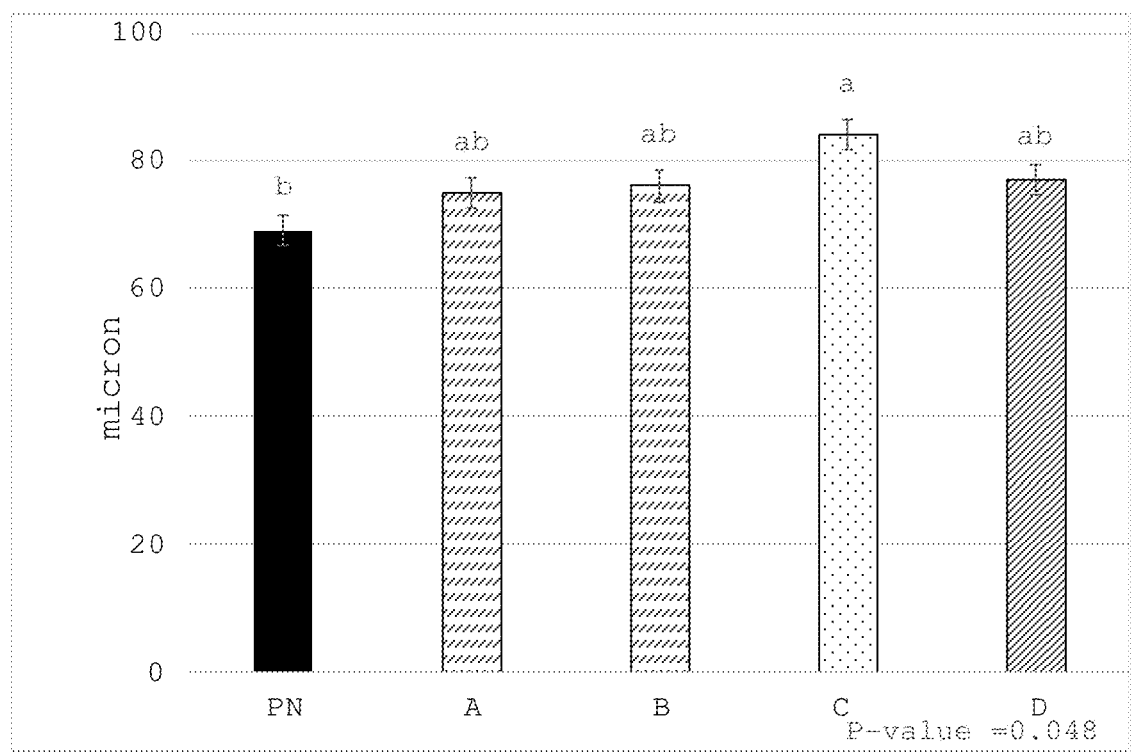
FIG. 12 shows the average colonic crypt depth for the respective Study Groups A, B, C and D (see Table 4) as well as Group P which is designated "PN" in this FIG. 12. Mean jejunal crypt depth in case of EN is 76p. Based on the analysis of data according to Fisher's LSD test, a significant difference was again found for Group C (arginine butyrate supplementation, 10 mmol/L TPN, AB-PN). Jejunal crypt depth was again lowest in Group P ("PN").

Formalin-fixed intestinal samples were embedded in paraffin, sliced to approximately 5-μm thickness with a microtome and stained with hematoxylin and eosin (FIG. 6). Villus height, midvillus width, and crypt depth were measured by using a Nikon Optiphot-2 microscope (Nikon, Melville, N.Y.) and ImagePro Express software (Version 4.5; Media Cybernetics, Inc, Silver Spring, Md.) in 8 to 10

3.3 Plasma Glucagon Like Peptide 2 (GLP-2) Concentrations

Plasma GLP-2 concentration is quantified by extracting plasma samples with 75% ethanol and centrifugation at 3000×g for 30 minutes at 4° C. The supernatant was decanted, lyophilized, and reconstituted to the original plasma volume in assay buffer (80 mmol/L $Na_3PO_4^-$, 0.01 mmol/L valine-pyrrolidide, 0.1% wt/vol human serum albumin, 10 mmol/L EDTA, 0.6 mmol/L thimerosal, pH 7.5). Approximately 300 μL of extracted samples and human GLP-2 standards are incubated with 100 μL of rabbit GLP-2 antiserum (final dilution 1:25,000) for 24 hours at 4° C., after which free and bound peptides are separated by absorption to plasma-coated charcoal (see also Bartholome et al, J Parent Nutr 2004; 28(4):210-223 for standards used). This antiserum is raised against the $NH_2$-terminal fragment of human GLP-2 and specifically recognizes the $NH_2$-terminal region of both human and porcine GLP-2.

3.4 IgA Quantification

Figure 13:
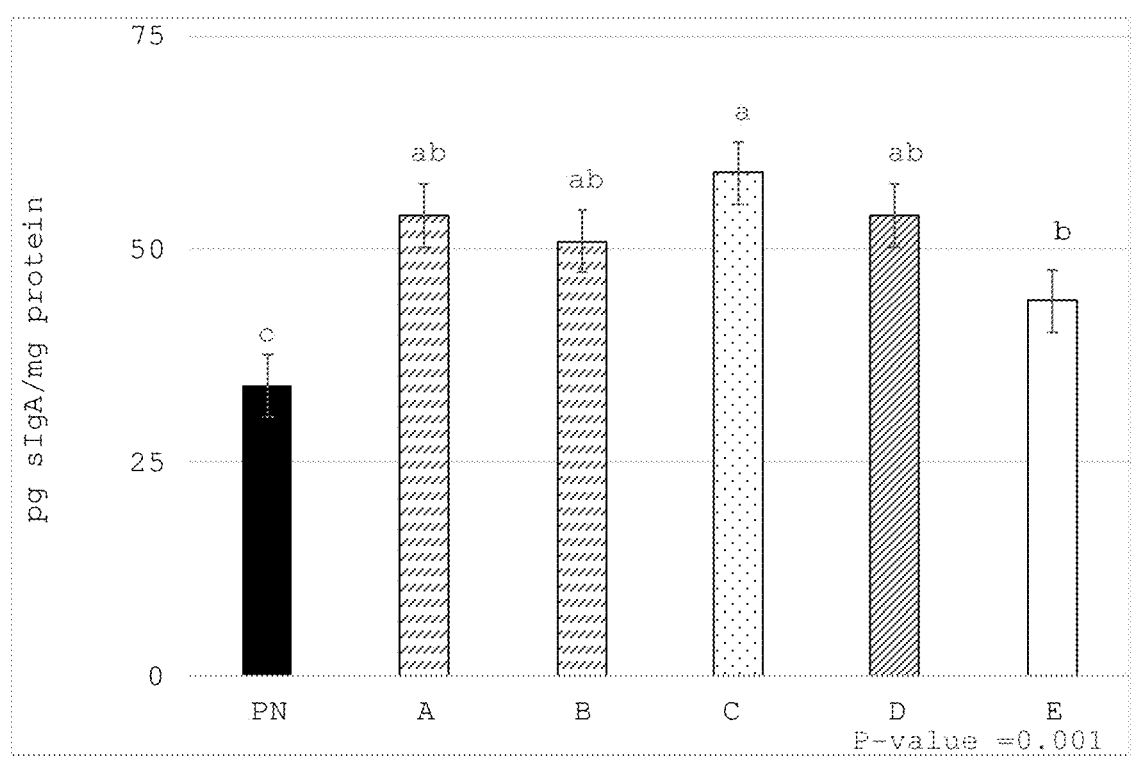
FIG. 13 shows the average jejunal sIgA concentration for the respective Study Groups A, B, C and D (see Table 4) as well as Group P which is designated "PN" in this FIG. 13. Based on the analysis of data according to Fisher's LSD test, a significant difference was again found for Group C (arginine butyrate supplementation, 10 mmol/L TPN, AB-PN), which was even more pronounced than for Group E, and even more pronounced than Group P ("PN").

Small intestine probes for IgA level determination were obtained by flushing the small intestine with chilled HBSS (Hank's Balanced Salt Solution). Nasal and bronchoalveolar washings for measurement of respiratory tract IgA levels were obtained by lavage with 1 mL phosphate-buffered saline solution under anesthesia. The washings were stored in a −80° C. freezer until IgA analysis. IgA was measured in small intestinal and respiratory tract washings by sandwich enzyme-linked immunosorbent assay using a polyclonal goat anti-mouse IgA (Sigma) to coat the plate, a purified mouse IgA (Zymed Laboratories, San Francisco, Calif.) as the standard, and a horseradish peroxidase-conjugated goat anti-mouse IgA (Sigma). Results are shown in FIG. 13.

3.5 Duodenal Mucosal Resistance

Duodenal mucosal resistance was determined according to known methods and according to Tappenden et al., Short-Chain Fatty Acid-Supplemented Total Parenteral Nutrition Enhances Functional Adaptation to Intestinal Resection in Rats. *Gastroenterology* 1997; 112:792-802. Pieces of intestine (1 cm$^2$) were cut out, and the tissue was mounted as flat sheets in incubation chambers containing oxygenated Krebs' bicarbonate buffer (pH 7.4) at 37° C. Tissue discs were preincubated in this buffer for 15 minutes to allow equilibration at this temperature. After preincubation, the chambers were transferred to other beakers containing [$^3$H]inulin and various 14C probe molecules in oxygenated Krebs' bicarbonate (pH 7.4 and 37° C.). The concentration of solutes was 4, 8, 16, 32, or 64 mmol/L for D-glucose and 16 mmol/L for L-glucose. The preincubation and incubation solutions were mixed at identical stirring rates with circular magnetic bars, and the stirring rates were adjusted by means of a strobe light. A stirring rate of 600 rpm was selected to achieve low effective resistance of the intestinal unstirred water. The experiment was terminated by removing the chambers and quickly rinsing the tissue in cold saline for approximately 5 seconds. The exposed mucosal tissue was then cut out of the chamber with a circular steel punch. For all probes, the tissue was dried overnight in an oven at 55° C. The dry weight of the tissue was determined, the sample was saponified with 0.75N NaOH, scintillation fluid was added (Beckman Ready Solv HP; Beckman, Mississauga, ON), and radioactivity was determined by means of volume of an external standardization technique to correct for variable quenching of the two isotopes. The mucosal weight was determined after scraping of the intestine from adjacent samples not used for uptake studies. The weight of the mucosa in the samples used to measure uptake was determined by multiplying the dry weight of the intestinal sample by the percentage of the intestinal wall comprised of mucosa. Results of the measurements for all Groups are provided in Table 7.

It was found that the Intervention Groups A, B, C and D, are significantly different from the P (S-PN) reference group (see Table 2) as regards duodenal mucosal resistance. Moreover, all interventions groups were not inferior or statistically different from Group E (enteral feeding). Intervention Group D resulted in duodenal resistance which is almost as good as in Group E (enteral). Remarkably, Group C showed a significantly lower loss of mucosal resistance compared to the other intervention groups, and is even better than the enteral Group E, indicating that the addition of arginine butyrate is surprisingly effective in maintaining or supporting duodenal mucosal resistance and improved gut health, including a low susceptibility for local inflammation.

TABLE 7

Mean duodenal mucosal resistance in the respective intervention Groups A-D, compared with S-PN (standard PN) and EN (enteral nutrition), as determined by Fisher's Least Significant Difference (LSD) Test. Group C (AB-PN) shows a significantly better resistance in comparison to other intervention groups and enteral nutrition Group E.

| Group Assignment | N | Mean | Grouping |
|---|---|---|---|
| P | 12 | 34.2533 | a |
| A | 12 | 21.8442 | ab |
| B | 12 | 16.0234 | ab |
| D | 12 | 15.8264 | ab |
| E | 13 | 15.2746 | b |
| C | 12 | 8.2593 | b |

3.6 Cytokine Quantification

Figure 15:
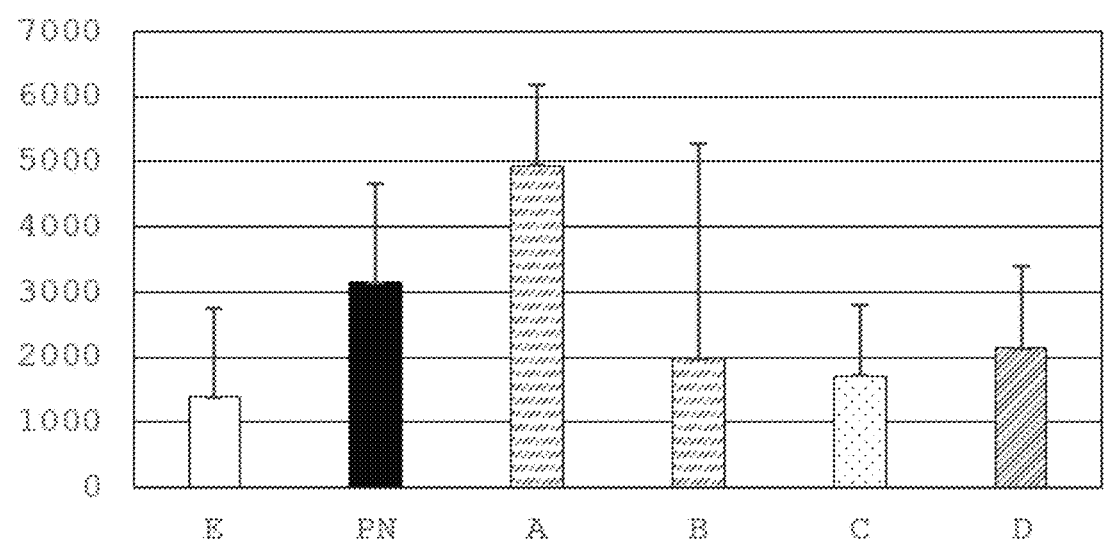
FIG. 15 shows serum levels of 11-6 in pg per ml serum found in the respective Study Groups A, B, C, D and E (see Table 4) as well as Group P which is designated "PN" in this FIG. 15. It can be seen that Group E is lowest, but that the average 11-6 concentration in Group C is significantly lower than in the standard PN group, and also lower compared to other Study (or intervention) Groups.
Figure 16:
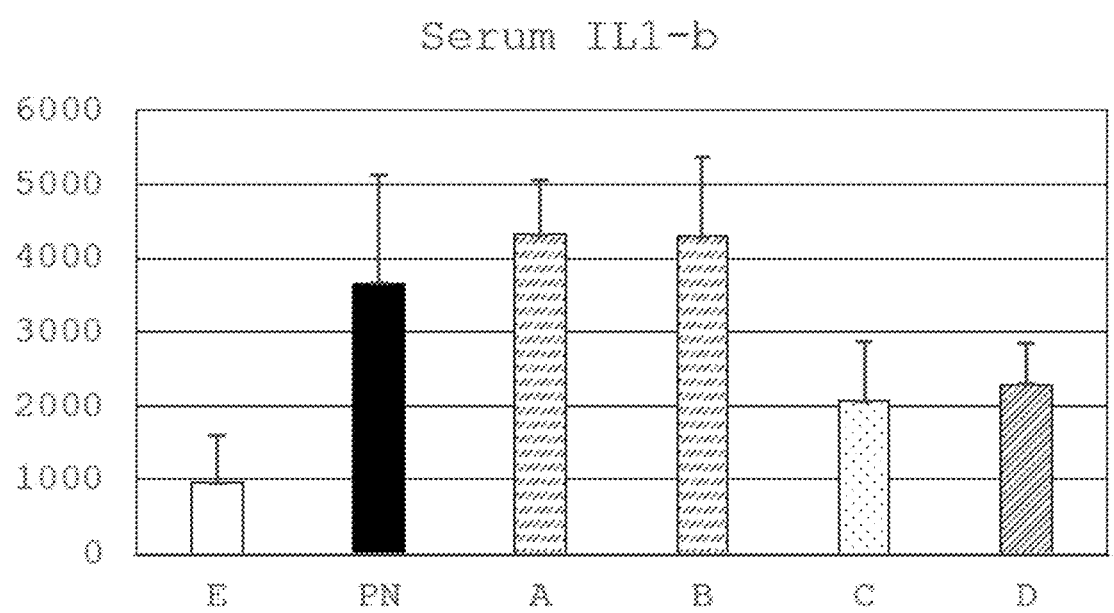
FIG. 16 shows serum levels of Il1-beta ("Il1-b") in pg per ml serum found in the respective Study Groups A, B, C, D and E (see Table 4) as well as Group P which is designated "PN" in this FIG. 15. It can be seen that Group E is lowest, but that the average Il1-beta concentration in Group C is again significantly lower than in the standard PN group, and also lower compared to other Study (or intervention) Groups.
Figure 17:
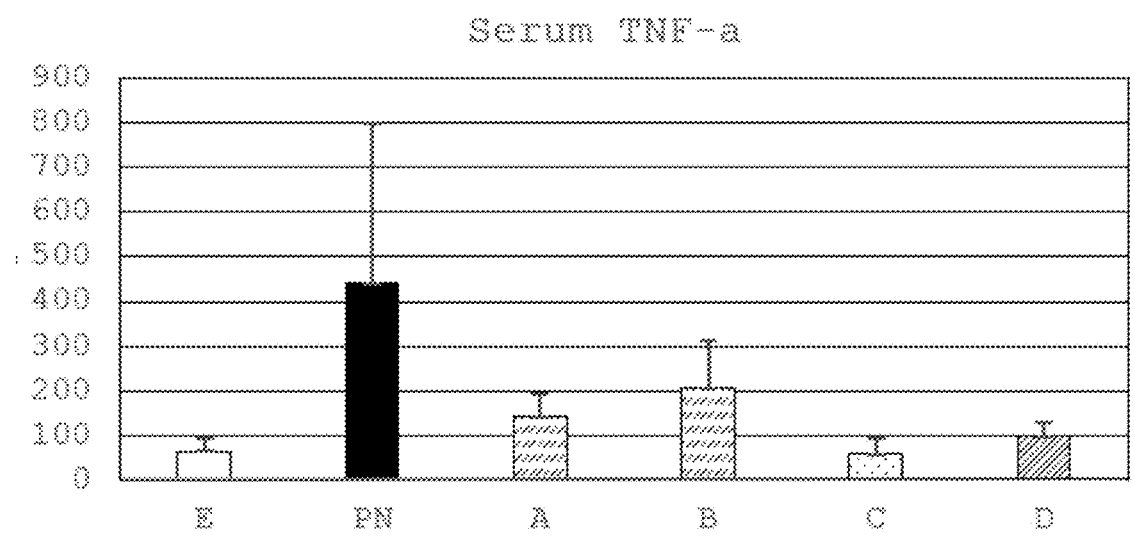
FIG. 17 shows serum levels of TNF-alpha ("TNF-a") in pg per ml serum found in the respective Study Groups A, B, C, D and E (see Table 4) as well as Group P which is designated "PN" in this FIG. 15. The TNF-alpha concentration in Study Group C is again lower than in the other Study (or intervention) Groups and result in about the same values as Group E.
Figure 18:
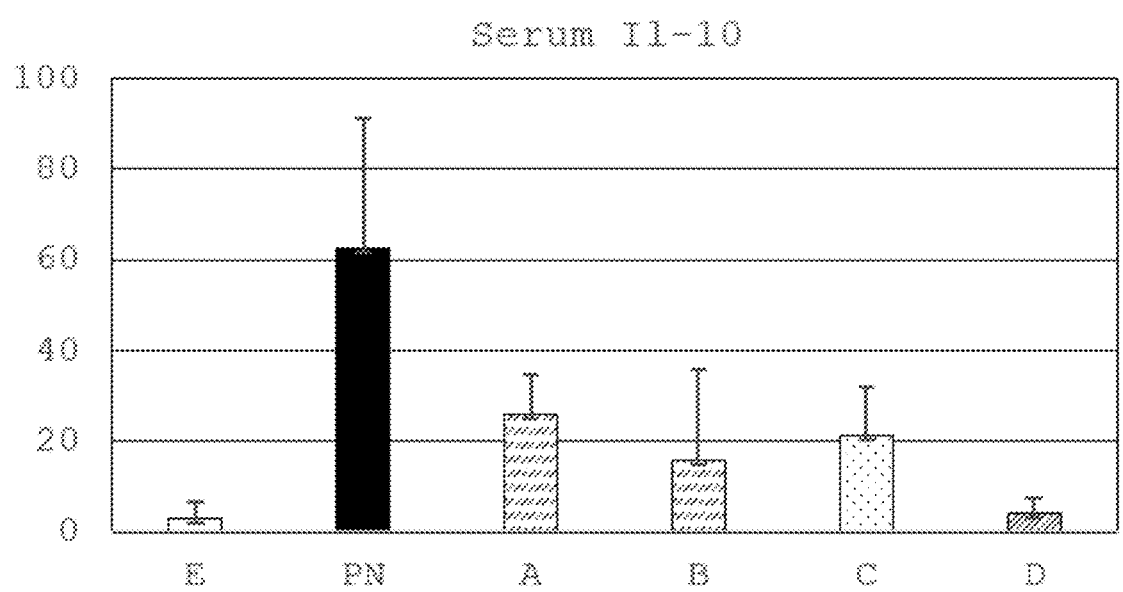
FIG. 18 shows serum levels of Il-10 in pg per ml serum found in the respective Study Groups A, B, C, D and E (see Table 4) as well as Group P which is designated "PN" in this FIG. 15. The TNF-alpha concentration in Study Group E is again lower than in the other Study (or intervention) Groups. Il-a0 concentration are almost or about as low in Study (or intervention) Group D. Study Groups A, B and C have all Il-10 concentrations which are lower than in the standard PN Group P.

The influence of the respective supplements on systemic inflammation was investigated by determining Il-6, Il-1beta, TNF-alpha and Il-10 serum levels in the intervention groups compared to EN and PN according to Milo et al., Effects of Short-Chain Fatty Acid-Supplemented Total Parenteral Nutrition on Intestinal Pro-Inflammatory Cytokine Abundance. *Digestive Diseases and Sciences* 2002; 47:2049-2055. Jejunal and ileal samples were homogenized in double-distilled water, and the Bradford protein assay (Biorad, Hercules, Calif., USA) was performed on homogenate and plasma samples. Protein (30 µg) from each sample was denatured by boiling, and proteins were separated by size using 12.5% sodium dodecyl sulfate polyacrylamide gel electrophoresis. Separated proteins were transferred to polyvinylidene difluoride membranes (Biorad) using a semidry transfer apparatus (Biorad). Western blot analysis for TNF-alpha, IL-1beta, Il-10 and IL-6 was performed using porcine-specific polyclonal antibodies (Endogen, Woburn, Mass., USA). A mouse anti-pig monoclonal TNF-alpha antibody was used to detect TNF-alpha (17,000 kDa). Rabbit anti-pig polyclonal antibodies specific for IL-1beta and IL-6 were used to detect IL-1beta (17,500 kDa), Il-10 (18,600 kDa) and IL-6 (26,000 kDa). Membranes were developed using the Opti-4CN kit (Biorad) and photographed using the FOTO/Analyst Image Analysis System (Fotodyne, Inc., Hartland, Wis., USA). Densitometry of TNF-alpha, IL-1beta, IL6, and Il-10 was performed using Collage Image Analysis Software 4.0 (Fotodyne, Inc.). Results are shown in FIG. 15 (Il-6), FIG. 16 (Il1-beta), FIG. 17 (TNF-alpha) and FIG. 18 (Il-10).

The invention claimed is:

1. A multi-chamber container for parenteral administration, comprising:
    (i) a carbohydrate formulation present in a first chamber; and
    (ii) an amino acid formulation present in a second chamber;
    wherein at least the first or the second chamber comprises arginine butyrate.

2. The multi-chamber container according to claim 1, additionally comprising:
    (iii) a lipid formulation present in a third chamber;
    wherein at least one of the first, the second chamber or the third chamber comprises arginine butyrate.

3. The multi-chamber container according to claim 1, wherein the arginine butyrate is present in a concentration of from 1 mmol to 300 mmol per liter of reconstituted multi-chamber container.

4. The multi-chamber container according to claim 1, wherein the arginine butyrate is present in the amino acid formulation of the second chamber.

5. The multi-chamber container according to claim 1, wherein the amino acid formulation comprises an aqueous solution of one or more amino acids, dipeptides and/or oligopeptides, and optionally one or more electrolytes selected from the group of electrolytes comprising sodium, potassium, magnesium, calcium, phosphate compounds, and contains multivalent anions of organic acids consisting of malate, citrate, acetate, lactate, gluconate, glucoheptonate, glucono-glucoheptonate, glucose-phosphate or inorganic acids consisting of sulfate, chloride.

6. The multi-chamber container according to claim 1, wherein the amino acid formulation comprises about 1 g to 30 g of amino acids per 100 mL of the amino acid formulation.

7. The multi-chamber container according to claim 1, wherein the arginine butyrate is present in the carbohydrate formulation of the first chamber.

8. The multi-chamber container according to claim 1, wherein the carbohydrate formulation comprises from 1 g to 100 g of glucose and/or maltose and/or trehalose per 100 mL of carbohydrate formulation, and optionally one or more electrolytes selected from the group of electrolytes consisting of sodium, potassium, magnesium, calcium, phosphate or glycerophosphate.

9. The multi-chamber container according to claim 2, wherein the arginine butyrate is present in the lipid formulation of the third chamber.

10. The multi-chamber container according to claim 2, wherein the lipid formulation comprises an aqueous phase and oil phase in an amount of from 1 g to 40 g of oil per 100 ml of lipid formulation.

11. The multi-chamber container according to claim 2, wherein the lipid formulation comprises at least one pharmaceutically acceptable antioxidant selected from the group consisting of alpha-tocopherol, beta-tocopherol, gamma-tocopherol, delta-tocopherol, tocotrienols, ascorbyl palmitate and ascorbic acid.

12. The multi-chamber container according to claim 10, wherein the oil phase comprises one or more oils selected from the group consisting of olive oil, soybean oil, safflower oil, coconut oil, fish oil, fish oil extract, krill oil, medium-chain triglycerides (MCTs), algae oil, fungi oil, corn oil, sunflower oil, palm kernel oil, and rapeseed oil.

13. The multi-chamber container according to claim 1, wherein at least one of the first chamber, the second chamber and the third chamber further comprise vitamins and/or trace elements.

14. The multi-chamber container according to claim 1, wherein the multi-chamber container comprises at least one further chamber containing a vitamin and/or trace element formulation.

15. The multi-chamber container according to claim 1, wherein arginine butyrate is present in a concentration of from 1 mmol to 300 mmol per liter of reconstituted multi-chamber container.

16. The multi-chamber container according to claim 2, wherein the lipid formulation in the third chamber comprises tributyrin in a concentration of from 1 mmol to 300 mmol per liter of reconstituted multi-chamber container, and wherein the total concentration of equivalent butyric acid does not exceed 301 mmol per liter of reconstituted multi-chamber container.

17. The multi-chamber container according to claim 16, wherein the arginine butyrate is present in the amino acid chamber.

18. The multi-chamber container according to claim 1, wherein the pH of a reconstituted formulation comprising the carbohydrate formulation from the first chamber and the amino acid formulation from the second chamber of the multi-chamber container is from 4.5 to 8.0.

19. An amino acid formulation for parenteral administration, wherein the amino acid formulation comprises arginine butyrate in a concentration of from 1 mmol to 300 mmol per liter of the amino acid formulation.

20. The amino acid formulation according to claim 19, wherein arginine butyrate is present in a concentration of from 1 mmol to 300 mmol per liter of the amino acid formulation, from 5 mmol to 300 mmol per liter of the amino acid formulation, from 1 mmol to 250 mmol per liter of the amino acid formulation, from 5 mmol to 125 mmol per liter of the amino acid formulation, from 5 mmol to 75 mmol per liter of the amino acid formulation, or from 5 mmol to 50 mmol per liter of the amino acid formulation.

21. The amino acid formulation according to claim 19, wherein the amino acid formulation comprises an aqueous solution of one or more amino acids selected from the group consisting of alanine (Ala), arginine (Arg), aspartic acid (Asp), glutamic acid (Glu), glutamine (Gln), glycine (Gly), histidine (His), leucine (Leu), isoleucine (Ile), lysine (Lys), methionine (Met), phenylalanine (Phe), proline (Pro), serine (Ser), threonine (Thr), tryptophan (Trp), tyrosine (Tyr), valine (Val), cysteine (Cys), ornithine (Orn), taurine, asparagine (Asn), Acetyl-cysteine (Ac-Cys), and Acetyl-tyrosine (Ac-Tyr); and optionally further comprises one or more electrolytes selected from the group consisting of sodium, potassium, magnesium, calcium, phosphate and glycerophosphate.

22. The amino acid formulation according to claim 19, wherein the formulation comprises one or more oligopeptides consisting of at least three amino acids and/or dipeptides selected from the group consisting of Acetyl-Tyrosine (Ac-Tyr), Alanyl-glutamine (Ala-Gln), Glycyl-glutamine (Gly-Gln), glycyl-tyrosine (Gly-Tyr) and Alanyl-Tyrosine (Ala-Tyr).

23. The amino acid formulation according to claim 19, wherein the formulation comprises one or more anions of organic acids selected from the group consisting of malate, citrate, acetate, lactate, gluconate, glucoheptonate, glucono-glucoheptonate, glucose-phosphate, and/or an inorganic acid selected from sulfate and chloride.

24. The amino acid formulation according to claim 19, wherein the formulation comprises about 1 g to 30 g of amino acids per 100 mL of the amino acid formulation.

25. The amino acid formulation according to claim 19, wherein the formulation comprises from 20 mg to 25 g choline equivalent per liter of amino acid formulation selected from the group consisting of choline chloride, choline bitartrate, choline citrate, choline gluconate, choline malate, choline cytidine diphosphate (CDP) salt and glycerophosphocholine (GPC).

26. The amino acid formulation according to claim 19, wherein the amino acid formulation further comprises vitamins and/or trace elements.

27. A composition reconstituted from a multi-chamber container according to claim 1 or an amino acid formulation according to claim 19 for parenteral administration to a patient who requires parenteral nutrition when oral and enteral nutrition is not possible, insufficient or contraindicated.

28. The composition for parenteral administration according to claim 27, wherein the patient is a pediatric or an adult patient.

29. The composition for parenteral administration according to claim 27, wherein the patient is selected from the group consisting of an intensive care patient, a critically ill patient on short-term parenteral nutrition who is covering 95-100% of the energy needs from parenteral nutrition, a patient suffering from sepsis or septic shock, a short bowel patient, an extreme short bowel patient, an intestinal failure patient, a metabolically stressed patient, an immunodeficient patient, a cancer patient, a cachexia patient, a malnourished patient, a patient suffering from or being at risk of developing reduced gut barrier, of hyperglycemia and/or hypertriglyceridemia, a critically ill patient for whom enteral nutrition is contraindicated, surgical/post-operative patients with sustained ileus or sustained nothing by mouth (NPO) status, a patient with entero-cutaneous fistula, a preterm infant, and a home parenteral nutrition (HPN) patient who is covering 95-100% of the energy needs from parenteral nutrition.

30. The composition for parenteral administration according to claim 27, wherein the patient suffers from or is at risk of developing systemic inflammation and/or local inflammation in the gut.

31. The composition for parenteral administration according to claim 27 for sustaining or improving local immunity in the gut and/or lung of a patient.

32. A method of treating patients who require parenteral nutrition when oral and enteral nutrition is not possible, insufficient or contraindicated with a composition reconstituted from a multi-chamber container according to claim 1 or an amino acid formulation according to claim 19.

33. The method according to claim 32, wherein the patient is a pediatric or an adult patient.

34. The method according to claim 32, wherein the patient is selected from the group consisting of an intensive care patient, a critically ill patient on short-term parenteral nutrition who is covering 95-100% of the energy needs from parenteral nutrition, a patient suffering from sepsis or septic shock, a short bowel patient, an extreme short bowel patient, an intestinal failure patient, a metabolically stressed patient, an immunodeficient patient, a cancer patient, a cachexia patient, a malnourished patient, a patient suffering from or being at risk of developing a reduced gut barrier, of hyperglycemia and/or hypertriglyceridemia, a critically ill patient for whom enteral nutrition is contraindicated, surgical/post-operative patients with sustained ileus or sustained nothing by mouth (NPO) status, patients with entero-cutaneous fistulas, a preterm infant, and a home parenteral nutrition (HPN) patient who is covering 95-100% of the energy needs from parenteral nutrition.

35. The composition for parenteral administration according to claim 27, wherein the patient suffers from or is at risk of developing systemic inflammation and/or local inflammation in the gut.

36. The method according to claim 32, wherein the patient suffers from systemic inflammation and/or local inflammation in the gut.

37. The method according to claim 32 for sustaining or improving local immunity in the gut and/or lung.

38. The method of claim 32, wherein the composition is administered to the patient to arrive at an arginine butyrate dose of from 5 mg/kg/day to 10 g/kg/day.

39. The method of claim 32, wherein the composition is administered to the patient to arrive at an arginine butyrate dose of from 5 mg/kg/day to 5 g/kg/day.

* * * * *